(12) United States Patent
Fateh

(10) Patent No.: US 11,081,218 B2
(45) Date of Patent: Aug. 3, 2021

(54) METHOD AND APPARATUS FOR VERIFYING THERAPEUTIC COMPLIANCE

(71) Applicant: KALI CARE, INC., Mountain View, CA (US)

(72) Inventor: Sina Fateh, Mountain View, CA (US)

(73) Assignee: KALI CARE, INC., Santa Clara, CA (US)

(*) Notice: Subject to any disclaimer, the term of this patent is extended or adjusted under 35 U.S.C. 154(b) by 985 days.

(21) Appl. No.: 14/686,319

(22) Filed: Apr. 14, 2015

(65) Prior Publication Data

US 2015/0302174 A1  Oct. 22, 2015

Related U.S. Application Data

(60) Provisional application No. 61/981,203, filed on Apr. 18, 2014.

(51) Int. Cl.
*G06Q 50/00* (2012.01)
*G16H 20/10* (2018.01)
(Continued)

(52) U.S. Cl.
CPC ............ *G16H 20/10* (2018.01); *G16H 20/30* (2018.01); *G16H 20/40* (2018.01)

(58) Field of Classification Search
CPC  A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20;
(Continued)

(56) References Cited

U.S. PATENT DOCUMENTS 6,032,119 A * 2/2000 Brown ................. G16H 40/63
705/2
2007/0123772 A1 * 5/2007 Euliano ................ G16H 20/10
600/407
(Continued)

OTHER PUBLICATIONS

Korostelev, M., et al., "M2-Pass: SMS-based Mobile Patient Support and Responding to Challenges of Transitional Care", 7th International Conference on Biomedical Engineering and Informatics, Dalian, doi: 10.1109/BMEI.2014.7002875, 2014, pp. 762-768.

*Primary Examiner* — Michael Tomaszewski
(74) *Attorney, Agent, or Firm* — Perkins Coie LLP

(57) ABSTRACT

An identity standard (a name, cell number, face image, etc.), a therapeutic event standard associated with the identity standard (such as a stored image of a person taking a medication), and a parameter standard associated with the identity standard (e.g. a time range for taking medication) are established. If a transmission (such as a selfie from a cell phone) is observed, that transmission is received and determinations are made as to whether the transmission satisfies the identity standard, the therapeutic event standard, and the parameter standard. If the identity standard, therapeutic event standard, and parameter standard are satisfied, a satisfaction reaction is executed (logging data, sending a confirmation message, etc.).

48 Claims, 11 Drawing Sheets

(51) Int. Cl.
*G16H 20/30* (2018.01)
*G16H 20/40* (2018.01)
*G06Q 10/00* (2012.01)

(58) Field of Classification Search
CPC ........ G16H 10/40; G16H 10/60; G16H 10/65;
G16H 15/00; G16H 20/00; G16H 20/10;
G16H 20/13; G16H 20/17; G16H 20/30;
G16H 20/40; G16H 20/60; G16H 20/70;
G16H 20/90; G16H 30/00; G16H 30/20;
G16H 30/40; G16H 40/00; G16H 40/20;
G16H 40/40; G16H 40/60; G16H 40/63;
G16H 40/67; G16H 50/00; G16H 50/20;
G16H 50/30; G16H 50/50; G16H 50/70;
G16H 50/80; G16H 70/00; G16H 70/20;
G16H 70/14; G16H 70/60; G16H 80/00
See application file for complete search history.

(56) References Cited

U.S. PATENT DOCUMENTS

| | | |
|---|---|---|
| 2008/0162393 A1* | 7/2008 | Iliff .................. G16H 40/67 706/46 |
| 2010/0203833 A1 | 8/2010 | Dorsey |
| 2011/0088003 A1 | 4/2011 | Swink et al. |
| 2012/0323589 A1 | 12/2012 | Udani |
| 2013/0240624 A1 | 9/2013 | Baym et al. |

* cited by examiner

METHOD AND APPARATUS FOR VERIFYING THERAPEUTIC COMPLIANCE

CLAIM OF PRIORITY

This application claims the benefit of U.S. Provisional Application Ser. No. 61/981,203 filed on Apr. 18, 2014, the contents of which are incorporated by reference for all intents and purposes.

FIELD OF THE INVENTION

This invention relates to the verification of compliance with therapeutic instructions, and collection of data therefor. More particularly, the invention relates to approaches for gathering data indicative of carrying out indicated therapeutic actions, and evaluating that data in such fashion as to enable confirmation that the therapeutic actions have indeed been carried out as indicated. The invention includes, but is not limited to, applications regarding patient compliance with instructions for taking medications.

DESCRIPTION OF RELATED ART

A number of medications and other therapeutic implements are available for treating various conditions. In certain cases, medications must be taken (and other therapeutic actions carried out) according to specific instructions in order to be safe and effective. For example, a certain medication may be most effective if taken every 12 hours, or if taken once a day at the same time, if taken with food, etc.

Conventionally, verifying whether medications are being taken as instructed, and in some cases whether medications are being taken at all, may be problematic. (This may likewise apply to other therapeutic actions.) The memories of patients, caregivers, and even medical professionals may not be reliable, particularly over long periods of time (e.g. for medications that must be taken for indefinite periods, such as certain glaucoma medications). While logs that are written, typed, etc. may enable more detailed verification, particularly over long periods, such logs also may have disadvantages, such as being cumbersome to use in daily life, subject to loss, forgotten like the medication itself, etc. In addition, a temptation may exist to back-date or otherwise alter logs to show a medication being taken even if it is uncertain whether the medication was indeed taken, or when it is known that the medication was not taken.

Records of therapeutic events that are incomplete, uncertain, or inaccurate can in turn contribute to difficulties in successfully carrying out the relevant therapies. For example, if glaucoma is progressing in a patient who has been instructed to take medication as a treatment, is the continued loss of vision due to a failure to take the medication as instructed, or to a failure to respond to the medication as expected? Assuming either answer to be true without adequate supporting information may itself be problematic. If it is assumed that the patient is taking the medication properly when he or she is not, increased doses, new medications, etc. may not address the progression of the glaucoma (and may come with side effects, increased cost, etc.). However, if it is assumed that the patient is not taking the medication properly when he or she is, the patient may suffer irreparable loss of vision due to inadequate medication.

BRIEF SUMMARY OF THE INVENTION

The present invention contemplates a variety of systems, apparatus, methods, and paradigms for verifying compliance with instructions for carrying out therapeutic events, and collection of data associated therewith.

In one embodiment of the present invention, a machine-implemented method is provided that includes establishing an identity standard, establishing a therapeutic event standard associated with the identity standard, and establishing a parameter standard associated with the identity standard. The method includes observing for a transmission. If the transmission is observed, the transmission is received. The method includes determining whether the transmission satisfies the identity standard, determining whether the transmission satisfies the therapeutic event standard, and determining whether the transmission satisfies the parameter standard. If the transmission satisfies the identity standard, the therapeutic event standard, and the parameter standard, a satisfaction reaction is executed.

The identity standard may include a received alphanumeric identifier matching a standard alphanumeric identifier. The identity standard may include a received name matching a name standard, a received address matching an address standard, a received social security number matching a social security number standard, a received medical records number matching a medical records number standard, a received password matching a password standard, a received email address matching an email address standard, and/or a received telephone number matching a telephone number standard.

The identity standard may include a received biometric substantially matching a biometric standard. The biometric standard may include a facial appearance standard, a voice pattern standard, a brainwave pattern standard, a retinal pattern standard, an iris pattern standard, and/or a cardiac pattern standard.

The therapeutic event standard may include receiving the transmission. The therapeutic event standard may include the transmission including content. The therapeutic event standard may include the transmission including text content, image content, sound content, and/or video content. The therapeutic event standard may include substantially matching the text content with a text content standard, the image content with an image content standard, the sound content with a sound content standard, and/or the video content with a video content standard.

The therapeutic event standard may include the content evidencing a therapeutic event. The therapeutic event standard may include the content depicting a therapeutic event. The therapeutic event standard may include the content including at least one image of at least a portion of the therapeutic event.

The therapeutic event may include administering a medication, utilizing a medical device, acquiring a medical status, performing an exercise, taking a break from an activity, and/or exiting an area. The therapeutic event may include administering an oral medication, administering an eye medication, administering a topical medication, administering an inhaled medication, and/or administering an injected medication.

The therapeutic event standard may include an image recognition standard. The therapeutic event standard may include a face recognition standard. The therapeutic event standard may include a medication recognition standard. The therapeutic event standard may include an action recognition standard. The therapeutic event standard may include a therapeutic action standard. The therapeutic event standard may include a medication administration standard.

The parameter standard may include a received time substantially matching a time standard. The parameter standard may include a received location substantially matching a location standard. The parameter standard may include a received medical condition substantially matching a medical condition standard. The parameter standard may include a received subject action substantially matching a subject action standard. The parameter standard may include a received environmental information substantially matching an environmental condition standard.

The transmission may include at least one of a text message, an image message, an audio message, and a video message. The transmission may be received wirelessly. The transmission may be received through a cellular network.

Determining whether the transmission satisfies the identity standard may include evaluating metadata of the transmission. Determining whether the transmission satisfies the identity standard may include evaluating a content of the transmission.

Determining whether the transmission satisfies the identity standard may include obtaining a received alphanumeric identifier from the transmission, and comparing the received alphanumeric identifier with the alphanumeric identifier standard. Determining whether the transmission satisfies the identity standard may include obtaining a received name, a received address, a received social security number, a received medical records number, a received password, a received email address, and/or a received telephone number from the transmission, and comparing the received name with the name standard, the received address with the address standard, the received social security number with the social security number standard, the received medical records number with the medical records number standard, the received password with the password standard, the received email address with the email address standard, and/or the received telephone number with the telephone number standard.

Determining whether the transmission satisfies the identity standard may include obtaining a received biometric from the transmission, comparing the received biometric with a biometric standard. The biometric standard may include a facial appearance of the subject, a voice pattern of the subject, a brainwave pattern of the subject, a retinal pattern of the subject, an iris pattern of the subject, and/or a cardiac pattern of the subject.

Determining whether the transmission satisfies the therapeutic event standard may include image recognition. Determining whether the transmission satisfies the therapeutic event standard may include face recognition. Determining whether the transmission satisfies the therapeutic event standard may include face recognition of a subject face in content of the transmission. Determining whether the transmission satisfies the therapeutic event standard may include face recognition of a subject face in image content of the transmission.

Determining whether the transmission satisfies the therapeutic event standard may include evaluating metadata of the transmission. Determining whether the transmission satisfies the therapeutic event standard may include evaluating a content of the transmission.

Determining whether the transmission satisfies the therapeutic event standard may include determining receipt of the transmission. Determining whether the transmission satisfies the therapeutic event standard may include determining whether the transmission includes content. Determining whether the transmission satisfies the therapeutic event standard may include determining whether the transmission includes text content, image content, sound content, and/or video content.

Determining whether the transmission satisfies the therapeutic event standard may include determining whether the text content substantially matches a text content standard, the image content substantially matches an image content standard, the sound content substantially matches a sound content standard, and/or the video content matches a video content standard.

Determining whether the transmission satisfies the therapeutic event standard may include determining whether the content evidences a therapeutic event. Determining whether the transmission satisfies the therapeutic event standard may include determining whether the content depicts a therapeutic event. Determining whether the transmission satisfies the therapeutic event standard may include determining whether the content includes at least one image of at least a portion of the therapeutic event.

The therapeutic event may include administering a medication, utilizing a medical device, acquiring a medical status, performing an exercise, taking a break from an activity, and exiting an area.

The therapeutic event may include at least one of administering an oral medication, administering an eye medication, administering a topical medication, administering an inhaled medication, and administering an injected medication.

Determining whether the transmission satisfies the therapeutic event standard may include image recognition. Determining whether the transmission satisfies the therapeutic event standard may include face recognition. Determining whether the transmission satisfies the therapeutic event standard may include face recognition of a subject face in content of the transmission. Determining whether the transmission satisfies the therapeutic event standard may include object recognition. Determining whether the transmission satisfies the therapeutic event standard may include object recognition of a medical implement in content of the transmission. Determining whether the transmission satisfies the therapeutic event standard may include object recognition of a medication in content of the transmission. Determining whether the transmission satisfies the therapeutic event standard may include face recognition of a subject face in content of the transmission, object recognition of a medication in content of the transmission, and the medication being proximate the subject face. Determining whether the transmission satisfies the therapeutic event standard may include action recognition. Determining whether the transmission satisfies the therapeutic event standard may include action recognition of a therapeutic event in content of the transmission.

The therapeutic event may include at least one of administering a medication, utilizing a medical device, acquiring a medical status, performing an exercise, taking a break from an activity, and exiting an area.

The therapeutic event may include at least one of administering an oral medication, administering an eye medication, administering a topical medication, administering an inhaled medication, and administering an injected medication.

Determining whether the transmission satisfies the therapeutic event standard may include face recognition of a subject face in content of the transmission, and action recognition of a therapeutic event in content of the transmission.

Determining whether the transmission satisfies the therapeutic event standard may include face recognition of a subject face in content of the transmission, object recognition of a medication in content of the transmission, and action recognition of a therapeutic event in content of the transmission, the therapeutic event comprising administration of a medication.

The therapeutic event may include administration of the medication by a subject of the subject face to the subject.

The content may include an image.

Determining whether the transmission satisfies the parameter standard may include evaluating metadata of the transmission. Determining whether the transmission satisfies the parameter standard may include evaluating a content of the transmission. Determining whether the transmission satisfies the parameter standard may include determining whether a time in the transmission substantially matches a time standard. Determining whether the transmission satisfies the parameter standard may include determining whether a transmission time of the transmission substantially matches a time standard. Determining whether the transmission satisfies the parameter standard may include determining whether a content creation time of content of the transmission substantially matches a time standard. Determining whether the transmission satisfies the parameter standard may include determining whether a location in the transmission substantially matches a location standard. Determining whether the transmission satisfies the parameter standard may include determining whether a transmission source location of the transmission substantially matches a location standard. Determining whether the transmission satisfies the parameter standard may include determining whether a content creation location of content of the transmission substantially matches a location standard. Determining whether the transmission satisfies the parameter standard may include determining whether a medical condition in the transmission substantially matches a medical condition standard. Determining whether the transmission satisfies the parameter standard may include determining whether an environmental condition in the transmission substantially matches an environmental condition standard. Determining whether the transmission satisfies the parameter standard may include determining whether an environmental condition in the transmission substantially matches an environmental condition standard. Determining whether the transmission satisfies the parameter standard may include image recognition. Determining whether the transmission satisfies the parameter standard may include object recognition. Determining whether the transmission satisfies the parameter standard may include action recognition.

The satisfaction reaction may include recording in a data store a satisfaction of the identity standard, the therapeutic event standard, and the parameter standard. The satisfaction reaction may include recording in a data store at least a portion of a content of the transmission. The satisfaction reaction may include comprises recording in a data store at least a portion of metadata of the transmission.

The satisfaction reaction comprises outputting a satisfaction response. The satisfaction response comprises at least a portion of a content of the transmission. The satisfaction response comprises at at least a portion of a content of the transmission. The satisfaction response comprises at least a portion of metadata of the transmission.

The method may include outputting the satisfaction response to the subject. The method may include outputting the satisfaction response to at least one of a caregiver of the subject, a medical entity, a research entity, an insurance entity, a regulatory entity, and a data storage entity. The method may include outputting the satisfaction response wirelessly. The method may include outputting the satisfaction response through a cellular network.

The method may include, if the transmission is not observed, executing a non-satisfaction reaction. The non-satisfaction reaction may include recording in a data store that the transmission is not observed. The non-satisfaction reaction may include recording in a data store non-satisfaction of the identity standard, the therapeutic event standard, and the parameter standard. The non-satisfaction reaction may include outputting a non-satisfaction response.

The method may include outputting the non-satisfaction response to the subject. The non-satisfaction response may include a reminder to the subject to establish the therapeutic event. The non-satisfaction response may include a reminder to the subject to send the transmission.

The method may include outputting the non-satisfaction response to at least one of a caregiver of the subject, a medical entity, a research entity, an insurance entity, a regulatory entity, and a data storage entity. The method may include outputting the non-satisfaction response wirelessly. The method may include outputting the non-satisfaction response through a cellular network.

The method may include, if the transmission does not satisfy at least one of the identity standard, the therapeutic event standard, and the parameter standard, executing a non-satisfaction reaction. The non-satisfaction reaction may include recording in a data store that the transmission is not observed. The non-satisfaction reaction may include recording in a data store non-satisfaction of the identity standard, the therapeutic event standard, and the parameter standard. The non-satisfaction reaction may include outputting a non-satisfaction response.

The method may include outputting the non-satisfaction response to the subject.

The non-satisfaction response may include a reminder to the subject to execute the therapeutic event. The non-satisfaction response may include a reminder to the subject to send the transmission.

The method may include outputting the non-satisfaction response to a caregiver of the subject, a medical entity, a research entity, an insurance entity, a regulatory entity, and/or a data storage entity.

The method may include outputting the satisfaction response wirelessly. The method may include outputting the satisfaction response through a cellular network.

In another embodiment of the present invention, an apparatus is provided, the apparatus including a processor, a receiver in communication with the processor, and an outputter in communication with the processor. The apparatus includes an establisher including executable instructions instantiated on the processor, the establisher being adapted to establish an identity standard, a therapeutic event standard associated with the identity standard, and a parameter standard associated with the identity standard. The apparatus includes a determiner including executable instructions instantiated on the processor, the determiner being adapted to determine whether a transmission satisfies the identity standard, the therapeutic event standard, and the parameter standard. The apparatus also includes a reactor including executable instructions instantiated on the processor, the responder being adapted to execute a satisfaction reaction if the transmission satisfies the identity standard, the therapeutic event standard, and the parameter standard.

The processor, the receiver, and the outputter may include a portable electronic device. The processor, the receiver, and the outputter may include a portable communication device. The processor, the receiver, and the outputter may include a computer server, desktop computer, a laptop computer, a tablet, a cell phone, and/or a head mounted display.

The apparatus may include an observer including executable instructions instantiated on the processor, the observer being adapted to observe a presence of the transmission.

The responder may be further adapted to execute a non-satisfaction reaction if the observer does not observe the presence of the transmission. The responder may be further adapted to execute a non-satisfaction reaction if the transmission does not satisfy at least one of the identity standard, the therapeutic standard, and the parameter standard.

The outputter may include a data store, a wireless transmitter, and/or a display.

The receiver may include a sensor, a wireless receiver, and/or a keypad.

In another embodiment of the present invention, an apparatus is provided, the apparatus including means for establishing an identity standard, means for establishing a therapeutic event standard associated with the identity standard, and means for establishing a parameter standard associated with the identity standard. The apparatus includes means for receiving a transmission. The apparatus also includes means for determining whether the transmission satisfies the identity standard, means for determining whether the transmission satisfies the therapeutic event standard, and means for determining whether the transmission satisfies the parameter standard. The apparatus further includes means for establishing a satisfaction reaction if the transmission satisfies the identity standard, the therapeutic event standard, and the parameter standard.

In another embodiment of the present invention a method is provided, including establishing an identity standard in a processor, establishing a therapeutic event standard associated with the identity standard in the processor, and establishing a parameter standard associated with the identity standard in said processor. The method also includes performing a therapeutic event, generating a transmission of the therapeutic event, and communicating the transmission to the processor. The method further includes determining in the processor whether the transmission satisfies the identity standard, determining in the processor whether the transmission satisfies the therapeutic event standard, and determining in the processor whether the transmission satisfies the parameter standard. The method also includes executing a satisfaction reaction with the processor if the transmission satisfies the identity standard, the therapeutic event standard, and the parameter standard, Generating the transmission of the therapeutic event may include capturing an image including the therapeutic event with a portable electronic device.

Generating the transmission of the therapeutic event may include capturing an image including the therapeutic event with a smart phone.

Generating the transmission of the therapeutic event may include capturing an image including the therapeutic event with a wearable electronic device.

Generating the transmission of the therapeutic event may include capturing an image including the therapeutic event with a wrist mounted device, the wrist mounted device including an imager disposed on the palm side of the wrist of the wearer thereof and including a field of view encompassing at least a portion of the palm of the wearer.

Generating the transmission of the therapeutic event may include capturing an image including the therapeutic event with a head mounted device, the head mounted device including an imager disposed on a forward aspect of the head of the wearer thereof and including a field of view encompassing at least a portion of a hand of the wearer.

In another embodiment of the present invention a method is provided, including establishing establishing in a processor an identity standard including a portable electronic device ID and a facial image, establishing in the processor a therapeutic event standard associated with the identity standard including an image of a medication, and establishing in the processor a parameter standard associated with the identity standard comprising a time. The method includes observing for a wireless transmission from a portable electronic device to the processor. The method also includes, if the transmission is observed, receiving the transmission in the processor, determining in the processor whether the transmission satisfies the identity standard, determining in the processor whether the transmission satisfies the therapeutic event standard, and determining in the processor whether the transmission satisfies the parameter standard. The method further includes executing in the processor a satisfaction reaction if the transmission satisfies the identity standard, the therapeutic event standard, and the parameter standard,

BRIEF DESCRIPTION OF THE SEVERAL VIEWS OF THE DRAWINGS

Like reference numbers generally indicate corresponding elements in the figures.

DETAILED DESCRIPTION OF THE INVENTION

Figure 1:
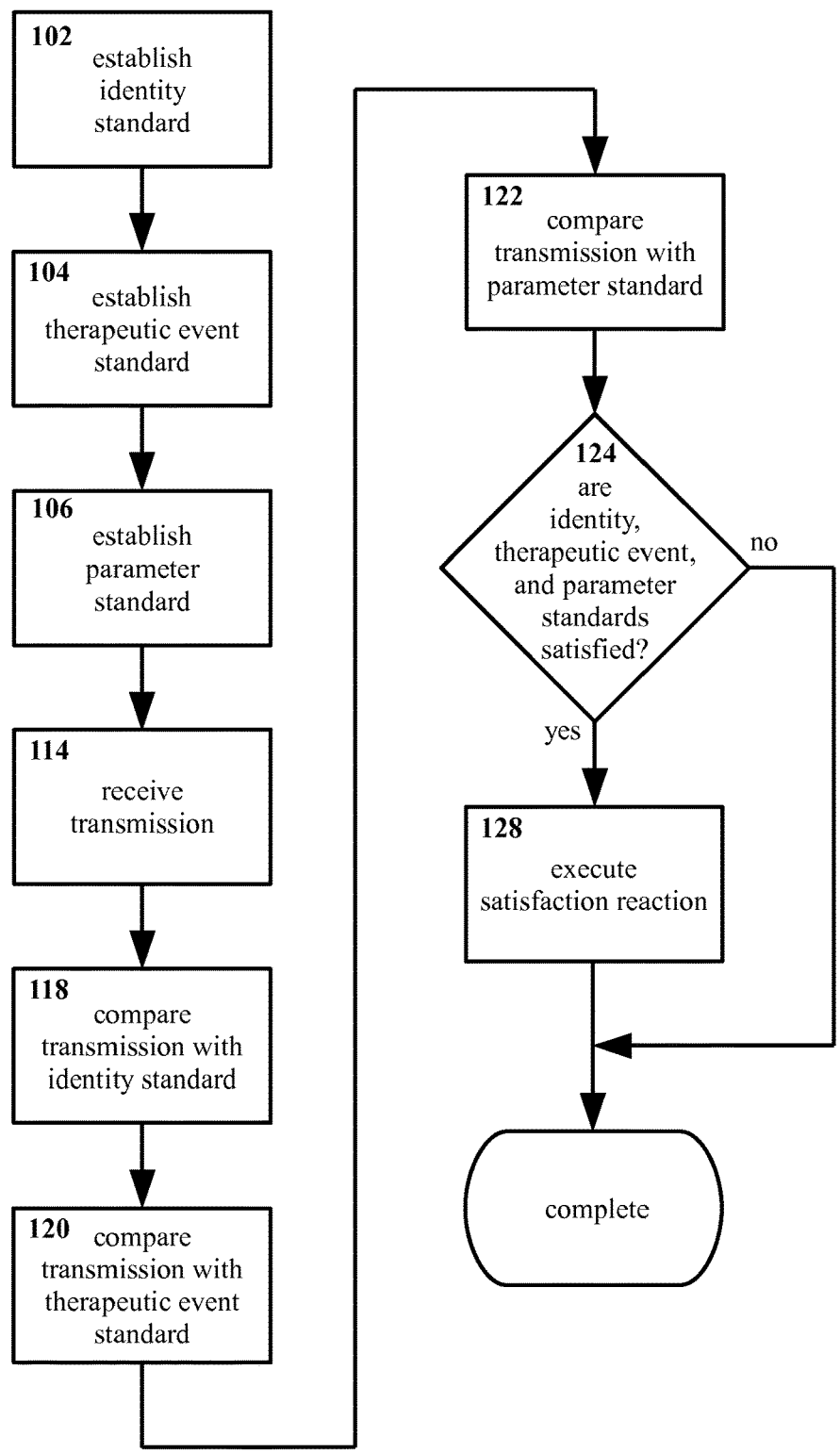
FIG. 1 shows an example embodiment of a method for verifying therapeutic compliance according to the present invention, in flow-chart form.

With reference to FIG. 1, therein is shown an example embodiment of a method for therapeutic verification according to the present invention.

In the example method of FIG. 1, an identity standard is established 102. An identity standard may be substantially any standard by which a subject may be identified. That is, an identity standard enables identification of a person or other entity, identification of a communication being from a person or entity, etc. Typically though not necessarily an identity standard may be a requirement that some sample information matches known information. For example, in the event that information for comparison were to be received by telephone, an identity standard may be a requirement that the telephone number from which a call in question is made matches a telephone number that is stored or otherwise available for comparison.

A wide range of information may be considered with regard to an identity standard. For example, identity standards may include matches of numerical and alphanumerical information such as names, addresses, social security numbers, medical records numbers, user names, passwords, email addresses, etc. Non-numerical information also may be considered. For example, identity standards may include matches of biometric information, such as facial images. Other biometric data that may be considered for an identity standard includes but is not limited to non-image facial information (e.g. geometry of various facial features, such as inter-pupillary distance), voice patterns, brainwave patterns, retinal patterns, iris patterns, cardiac patterns, etc.

In addition, while typically (though not necessarily) some degree of information match is incorporated into an identity standard, the degree of match, criteria constituting a match, etc. may vary. For example, a match of a received user name or password to a stored user name or password match may be required to be exact, while a match of a facial image may be required to be substantially similar, similar to 98% according to some mathematical algorithm for facial identification, etc.

Furthermore, for arrangements wherein an identity standard relates to entered data, transmitted data, etc., the identity standard may relate to the content of the message proper, and/or to metadata associated with the message. For example, an identity standard applicable to an image transmitted by a smart phone may relate to factors such the image itself (content), and/or to factors such as the telephone number of the smart phone sending the message (metadata).

An identity standard may include multiple factors. For example, an identity standard may require that a username and a password precisely match a stored username and password, and that a subject image substantially matches a stored subject image. Alternative standards likewise are permissible, e.g. a username and password must match a stored username and password, or a subject image substantially matches a stored subject image.

With regard to establishing the identity standard 102 (and with other steps described herein unless otherwise specified), the term "establish" should be understood broadly. In establishing an identity standard 102, the identity may be entered as data by a subject, read from from a hard drive, generated computationally in a processor, or otherwise in some fashion made available. The present invention is not particularly limited with regard to how any identity standard may be established.

Continuing in FIG. 1, a therapeutic event standard is established 104. A therapeutic event standard may be substantially any standard by which a therapeutic event may be identified as taking place. That is, a therapeutic event standard enables identification of the administration of a medication, the execution of a physical therapy exercise, etc. Typically though not necessarily an identity standard may be a requirement that some sample information matches known information. For example, a therapeutic event standard may be that a digital image of a subject administering a medication step substantially matches a stored image of the subject and/or a stored image of the medication.

Likewise, a therapeutic event itself may be substantially any event or action relating in some fashion to health, health maintenance, safety, etc. Typically, though not necessarily, a therapeutic event may relate to a particular individual subject (e.g. a patient receiving health care). Also typically, though again not necessarily, a therapeutic event is action that is necessary or desirable for health. For example, therapeutic events may include, but are not limited to, administering a medication, avoiding sunlight or pollen (e.g. for persons sensitive thereto), contacting a health professional, sensing some form of bio-information such as pulse rate or blood pressure, providing feedback, recording and/or transmitting data, measuring an environmental parameter such as temperature or air pressure, etc.

A therapeutic event may be negative. That is, not operating machinery for some period of time after taking a medication could constitute a therapeutic event.

The present invention is not particularly limited with regard to what may constitute a therapeutic event, and events other than those described may be equally suitable.

A wide range of information may be considered with regard to a therapeutic event standard. As noted above therapeutic events may vary considerably, and a particular therapeutic event standard may to at least some degree depend on the particulars of the relevant therapeutic event. Even for a given therapeutic event, therapeutic event standards may vary.

For example, a therapeutic event standard may be merely that some transmission or data is received, or that some other event takes place, without necessarily verifying that the transmission, data, event, itself explicitly confirms the execution of the therapeutic event. As a more concrete example, if a destination for text messages, voicemails, emails, etc. is arranged for a subject to report the execution of some therapeutic event (e.g. taking a medication), the simple receipt of a text message, voicemail, email, etc. may be considered sufficient evidence that the therapeutic event has indeed taken place regardless of the content of the text message, voicemail, email (or even regardless of whether any such content is present). Thus, a therapeutic standard may be merely that a transmission is received, that the transmission has content, that the transmission content is of a some broad type (text, image, sound, video, etc.).

However, some degree of evaluation of content of a transmission, and/or of metadata associated with the transmission, also may be considered with regard to a therapeutic event standard. Thus, to continue the example above if text content, image content, sound content, video content, etc. is to be received, the therapeutic event standard may consider some evaluation of that text content, image content, sound content, video content, in addition to or instead of the simple presence of such content.

When such evaluation is to be undertaken, a therapeutic event standard typically though not necessarily may include a requirement that the content depicts (e.g. in an image) or otherwise evidences (e.g. by providing blood levels of a medication) the therapeutic event in question.

With regard to a therapeutic event standard that corresponds with depicting a therapeutic event, as noted one such example may be the presence of an image showing at least a portion of the therapeutic event, and/or analysis of such an image. As a more concrete example, such a therapeutic standard may be that a received image substantially matches, as determined through image recognition analysis, action recognition analysis, etc., a stored image that shows some portion of a known therapeutic event (or stored data otherwise sufficient to determine that the received image does depict some portion of the therapeutic event). Examples of therapeutic events that may be considered in such fashion with regard to a therapeutic event standard include, but are not limited to administering a medication, utilizing a medical device, acquiring a medical status, performing an exercise, taking a break from an activity, and exiting an area.

Although for illustrative purposes therapeutic events considered for a therapeutic event standard may be described as broad classes, such therapeutic events may be more specifically defined for a given therapeutic event standard. For example, with regard more specifically to a therapeutic standard that considers an image of at least a portion of a therapeutic event, administering a medication may be further broken down as administering an oral medication, administering an eye medication, administering a topical medication, administering an inhaled medication, and administering an injected medication. Thus a single therapeutic event standard may potentially cover taking any medication orally, for example as determined through analysis of an image of a subject taking a medication. A therapeutic event standard may however be broader, e.g. taking any medication, or narrower, e.g. taking a specific medication (which consideration may include evaluating the color, size, and/or shape of a tablet visible in an image, recognizing markings on such a tablet, etc., recognizing or reading labels, bar codes, etc. visible in an image, etc.).

For an arrangement wherein a therapeutic event standard considers a particular type of information, such information typically will be addressed by the standard itself in some fashion. For example, a therapeutic event standard that considers an image may include an image recognition standard, in addition to or in place of any other specific requirements in the therapeutic information standard. The therapeutic event standard may, depending on the particulars of a given embodiment, incorporate an image recognition standard, a face recognition standard (e.g. a face in a received image substantially matches), a medication recognition standard (e.g. a medication in a received image substantially matches), an action recognition standard (e.g. an action in a received image substantially matches), a therapeutic action standard (e.g. a therapeutic action in a received image substantially matches), a medication administration standard (e.g. medication administration in a received image substantially matches), etc.

As noted with regard to step 102, establishing a therapeutic event standard 104 in FIG. 1 may include consideration of received content, and/or consideration of metadata.

Continuing in FIG. 1, a parameter standard is established 106. A parameter standard may be substantially any standard addressing some parameter of a therapeutic event, such as how the therapeutic event is performed, when, where, under what environmental conditions, under what medical conditions, by whom, etc.

Typically though not necessarily a parameter standard may be a requirement that some sample information matches known information. For example, a parameter standard may be that a therapeutic event (typically as defined by the therapeutic event standard) is executed within some stored time range, before or after some stored time, etc.

Parameters and standards therefor may vary widely. For example, even considering time as a parameter, a parameter standard may address the time at which a therapeutic event takes place, the time at which an image depicting the therapeutic event is captured/created, the time at which the image is received, etc. A time standard (as a parameter standard) may require a received time to precisely match a stored time, a received time to substantially match to a stored time, a received time to fall within a stored time range, etc.

Other parameters may include but are not limited to location, medical condition, subject action, and environmental information. Likewise, parameter standards may consider matching (or otherwise addressing) a stored location, a stored medical condition, a stored subject action, stored environmental information, etc., and/or a stored range for any such. It should be understood that in "receiving" (for example) a medical condition, the condition itself is not necessarily received, rather information regarding that condition may be received.

Again with reference to FIG. 1, a transmission is received 114. As is described below, the transmission is considered with regard to determining whether the identity standard, therapeutic event standard, and parameter standard are satisfied (as established in steps 102, 104, and 106 above). Thus typically the transmission may be some form of data transmission, e.g. with text content, image content, audio content, video content, etc. However, as noted above with regard to steps 102, 104, and 106 the identity, therapeutic event, and parameter standards may consider metadata, even to the exclusion of considering content, and thus a transmission that lacks any substantive content may for at least certain embodiments be equally suitable. The present invention is not particularly limited with regard to the form or content of the transmission.

Likewise, the present invention is not particularly limited with regard to the manner by which the transmission is received. For example, a transmission may be received by direct data entry, e.g. being keyed in to a processor through a keyboard, scanned with a scanner, etc. A transmission may be received through wired communication, such as by a land line telephone or fiber optic cable. A transmission may also be received wirelessly, for example through wifi, Bluetooth, or a cellular telephone/data network.

Moving on in FIG. 1, the transmission is compared with the identity standard 118. The manner of the comparison may vary, but typically will depend at least in part on the particulars of the identity standard itself. For example, a standard that requires a face in a received image to substantially match a stored image of a face typically may include analysis of a received image with face identification algorithms, etc. The present invention is not particularly limited with regard to how the transmission may be compared with the identity standard 118.

The transmission also is compared with the therapeutic event standard 120. Again, the manner of comparison may vary, but typically will depend at least in part on the particulars of the therapeutic event standard. For example, a standard that requires a medication in a received image to substantially match a stored image of a medication typically may include analysis of a received image with medication identification algorithms and/or other object identification algorithms. The present invention is not particularly limited with regard to how the transmission may be compared with the therapeutic event standard 120.

The transmission also is compared with the parameter standard 122. Again, the manner of comparison may vary, but typically will depend at least in part on the particulars of the parameter standard. For example, a standard that requires that a received image have a creation time within some stored time range typically may include numerical comparison of the creation time of the image (typically though not necessarily stored as metadata) with the stored time range. The present invention is not particularly limited with regard to how the transmission may be compared with the parameter standard 122.

Still with reference to FIG. 1, a determination is made 124 as to whether the identity standard, therapeutic event standard, and parameter standards are satisfied. This determination is made based on the standards as established in steps 102, 104, and 106 and the comparisons of the received transmission with those standards in steps 118, 120, and 122.

As has been noted previously with regard to steps already described, determining 124 whether the identity standard, therapeutic event standard, and parameter standard are satisfied may include consideration of the content of the transmission (if any), and/or metadata associated with the transmission (again, if any). The determination 124 (and/or comparison steps 118, 120, and 122 depending upon the embodiment) may include obtaining from the transmission any data and/or metadata relevant to the identity standard, therapeutic event standard, and parameter standard, and comparing that information to the identity standard, therapeutic event standard, and parameter standard.

If the determination 124 is negative—that is, if the transmission fails to satisfy one or more of the identity standard, the therapeutic event standard, and the parameter standard—then the method skips step 128 and is complete as shown in FIG. 1.

If the determination 124 is positive—if the transmission satisifes the identity standard, the therapeutic event standard, and the parameter standard—then the method continues with step 128.

In step 128, a satisfaction reaction is executed. The satisfaction reaction may be substantially any action responsive to a positive determination in step 124. Typically, though not necessarily, the satisfaction reaction may include either an action by and/or within a processor, and/or a transmission of information to some entity external to such a processor.

For example, the satisfaction reaction may include recording in a data store (such as a hard drive, solid state drive, cloud memory, etc.) that the identity standard, therapeutic event standard, and/or parameter standards have been satisfied. The satisfaction reaction similarly may store an acknowledgement that the transmission has been received, some or all of any metadata associated with the transmission, some or all of any content of the transmission, etc. Information regarding what analysis was performed (if any) on metadata and/or content, how the analysis was performed, the results thereof, etc. also may be recorded in a data store.

In addition to or instead of recording information, the satisfaction reaction may include sending a satisfaction response to some entity external to the processor. For example, a satisfaction response may be sent to the subject or other sender of the transmission, indicating that the transmission was received, that the identity standard, therapeutic event standard, and/or parameter standard are satisfied by the transmission, the time the transmission was received, etc.

The satisfaction reaction may include sending a satisfaction response to some entity other than the subject or sender of the transmission. For example, information may be sent to a medical care provider such as a physican or hospital, to a medical study database, to an insurance company, etc.

A satisfaction response may be simple (e.g. a small image acknowledging receipt of the transmission) or complex (detailed analysis of the information in the transmission). The satisfaction response may be sent in various manners depending on the particulars of a given embodiment. The satisfaction response may be sent by land line, fiber optic cable, wifi, Bluetooth, cellular telephone/data network, etc.

The present invention is not particularly limited with regard to the content or destination of the satisfaction response, or to the manner by which the satisfaction response is sent (if the satisfaction reaction is sent externally at all).

Likewise, the present invention is not particularly limited with regard to nature, method of execution, etc. of the satisfaction reaction overall (whether or not the satisfaction reaction includes a satisfaction response).

Although the arrangement in FIG. 1 shows the method being complete after step 128, this is an example only. Other steps, other functions, etc. may be incorporated into the method, and/or other methods may be executed in combination with the method according to the present invention, the method may repeat, etc.

Figure 2:
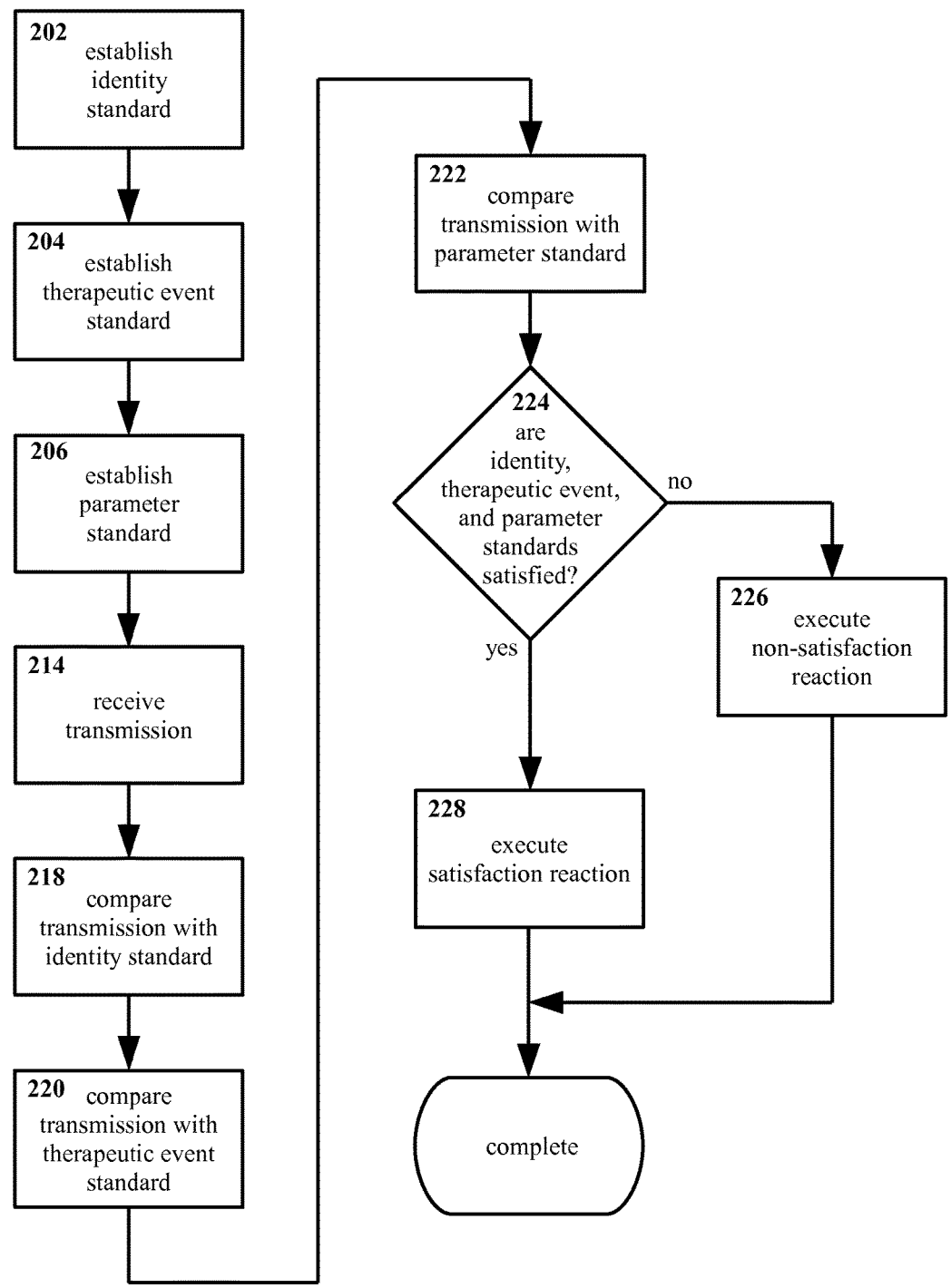
FIG. 2 shows another example embodiment of a method for verifying therapeutic compliance according the present invention, including a non-satisfaction reaction, in flow-chart form.

For example, with reference to FIG. 2 a method at least somewhat similar to that in FIG. 1 is shown. In the example method of FIG. 2, an identity standard is established 202, a therapeutic event standard is established 204, and a parameter standard is established 206. A transmission is received 214. The transmission is compared with the identity standard 218, compared with the therapeutic event standard 220, and compared with the parameter standard 222. A determination is made 224 as to whether the identity standard, therapeutic event standard, and parameter standards are satisfied by the transmission.

In the arrangement of FIG. 2, if the identity standard, therapeutic event standard, and parameter standards are satisfied by the transmission, then the method continues with executing a satisfaction reaction 228.

However, unlike FIG. 1, in FIG. 2 if one or more of the identity standard, therapeutic standard, and parameter standards are not satisfied by the transmission, then the method continues instead with executing a non-satisfaction reaction 226.

The non-satisfaction reaction may be substantially any action responsive to a negative determination in step 224. Typically, though not necessarily, the non-satisfaction reaction may include either an action by and/or within a processor, and/or a transmission of information to some entity external to such a processor.

For example, the non-satisfaction reaction may include recording in a data store (such as a hard drive, solid state drive, cloud memory, etc.) that the identity standard, therapeutic event standard, and/or parameter standards have not been satisfied. The non-satisfaction reaction similarly may store an acknowledgement that the transmission has been received, some or all of any metadata associated with the transmission, some or all of any content of the transmission, etc. Information regarding what analysis was performed (if any) on metadata and/or content, how the analysis was performed, the results thereof, etc. also may be recorded in a data store.

In addition to or instead of recording information, the non-satisfaction reaction may include sending a satisfaction response to some entity external to the processor. For example, a non-satisfaction response may be sent to the subject or other sender of the transmission, indicating that the transmission was received, that the identity standard, therapeutic event standard, and/or parameter standard are not satisfied by the transmission, the time the transmission was received, etc.

The non-satisfaction reaction may include sending a non-satisfaction response to some entity other than the subject or sender of the transmission. For example, information may be sent to a medical care provider such as a physican or hospital, to a medical study database, to an insurance company, etc.

A non-satisfaction response may be simple (e.g. a small image acknowledging receipt of the transmission) or complex (detailed analysis of the information in the transmission).

The non-satisfaction response may be sent in various manners depending on the particulars of a given embodiment. The non-satisfaction response may be sent by land line, fiber optic cable, wifi, Bluetooth, cellular telephone/data network, etc.

The present invention is not particularly limited with regard to the content or destination of the non-satisfaction response, or to the manner by which the non-satisfaction response is sent (if the non-satisfaction reaction is sent response at all).

Figure 3:
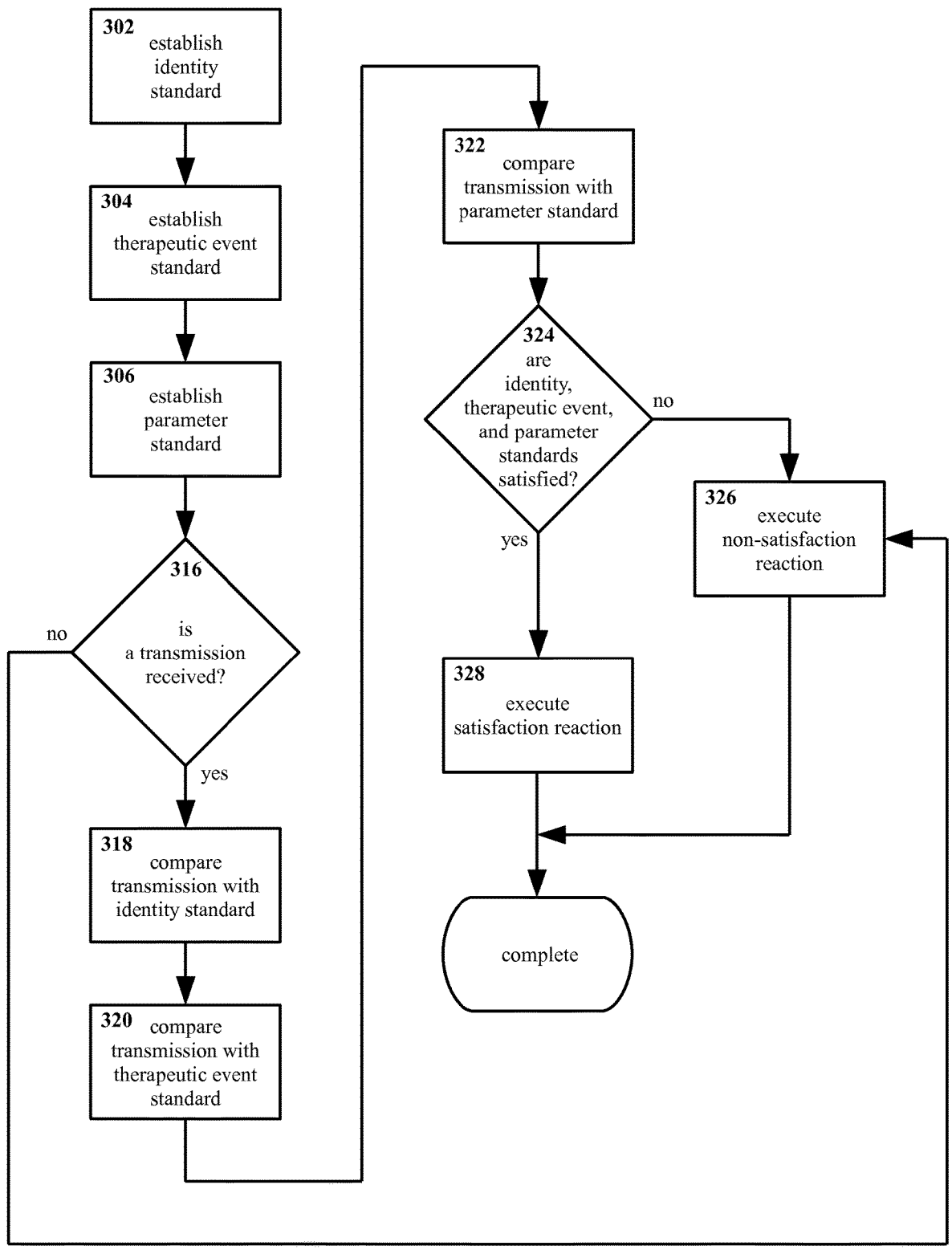
FIG. 3 shows another example embodiment of a method for verifying therapeutic compliance according the present invention, including consideration for absence of a transmission, in flow-chart form.

With reference now to FIG. 3, another example method for verifying therapeutic compliance according to the present invention is shown therein. Again, the example method in FIG. 3 bears at least some resemblance to the method in FIG. 1.

Likewise, the present invention is not particularly limited with regard to nature, method of execution, etc. of the non-satisfaction reaction overall (whether or not the non-satisfaction reaction includes a non-satisfaction response).

In the example method of FIG. 3, an identity standard is established 302, a therapeutic event standard is established 304, and a parameter standard is established 306.

However, where in FIG. 1 (and likewise FIG. 2) it was assumed for simplicity that a transmission is received, in FIG. 3 a determination is made 316 as to whether a transmission is received or not. For example, if a subject does not send a transmission, then it may be expected that no transmission will be received, and other factors (poor communication, etc.) likewise may affect whether a transmission is received.

If the determination 316 is negative—if a transmission is not received—then the method proceeds with executing a non-satisfaction reaction 326. Non-satisfaction reactions have already been described herein with regard to step 226 in FIG. 2, however, for arrangements such as that shown in FIG. 3 additional options may exist. For example, if no transmission is received, the non-satisfaction reaction may be to record in a data store that no transmission was received. The non-satisfaction reaction also may include sending a non-satisfaction response to the subject or other sender (or anticipated sender, e.g. based on the identity standard) indicating that a transmission was not received. Such a non-satisfaction response may, for example, serve as a reminder to take a medication, or otherwise perform some therapeutic event. Similarly, a non-satisfaction response as part of a non-satisfaction reaction may be sent to a medical care giver, a research database, etc.

If the determination is positive—if a transmission is received—then the method continues with comparing 318 the transmission with the identity standard, comparing 320 the transmission with the therapeutic event standard, and comparing 322 the transmission with the parameter standard.

Still with reference to FIG. 3, a determination is made 324 as to whether the identity standard, therapeutic event standard, and parameter standards are satisfied. This determination is made based on the standards as established in steps 302, 304, and 306 and the comparisons of the received transmission with those standards in steps 318, 320, and 322.

If the identity standard, therapeutic event standard, and parameter standards are satisfied by the transmission, then the method continues with executing a satisfaction reaction 328. If one or more of the identity standard, therapeutic standard, and parameter standards are not satisfied by the transmission, then the method continues instead with executing the non-satisfaction reaction 326. The non-satisfaction reaction for FIG. 3 has been described already herein. However, it is emphasized that the non-satisfaction reaction may be executed 326 in response to negative determinations in either of steps 316 and 324; either lack of a transmission or an unsatisfactory transmission may lead to execution 326 of the non-satisfaction reaction.

Now with regard to FIG. 4A through FIG. 4G, therein are illustrated example events as may be associated with one possible embodiment of a method for verifying therapeutic compliance according to the present invention. However, it is noted that not all actions shown necessarily are required for or part of a method according to the present invention. For example, although the user may take a medication, taking the medication may not itself be part of a method according to the present invention; rather the present invention may address determining whether medication is taken, and may be functional even if the medication is not taken (e.g. a determination may be made that therapeutic event standards are not satisfied).

In particular, FIG. 4A through FIG. 4G illustrates action as may be undertaken in executing a particular therapeutic action and capturing evidence thereof for transmission. In the example shown the therapeutic action is a subject administering an oral medication to himself/herself, and capturing an image thereof. However, although this example is presented to provide a concrete instance relating to the present invention, it is emphasized that the present invention is not limited only to arrangements relating to taking an oral medication, or otherwise specific to the example shown and described with respect to FIG. 4A through FIG. 4G In the arrangement of FIG. 4A, a subject 432A is shown therein, with the subject's face 434A visible. In particular, the subject's mouth 436A is visible, in a closed position. This may be considered a "neutral" or "starting" position for the example in FIG. 4A through FIG. 4G In FIG. 4B, a subject 432B is also shown therein with the subject's face 434B visible. The subject 432B has his/her mouth 436B open.

In FIG. 4C, a subject 432C is again shown with the subject's face 434C visible and mouth 436C open. In addition, the subject 432C has extended his/her tongue 438C.

Figure 4A:
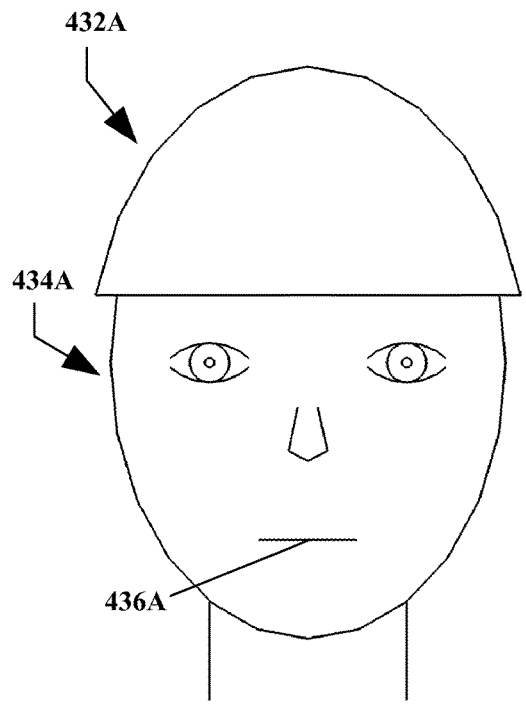
FIG. 4A through FIG. 4G show a sequence of events as may be associated with one example embodiment of a method for verifying therapeutic compliance according to the present invention, utilizing a smart phone or similar mobile device.
Figure 4B:
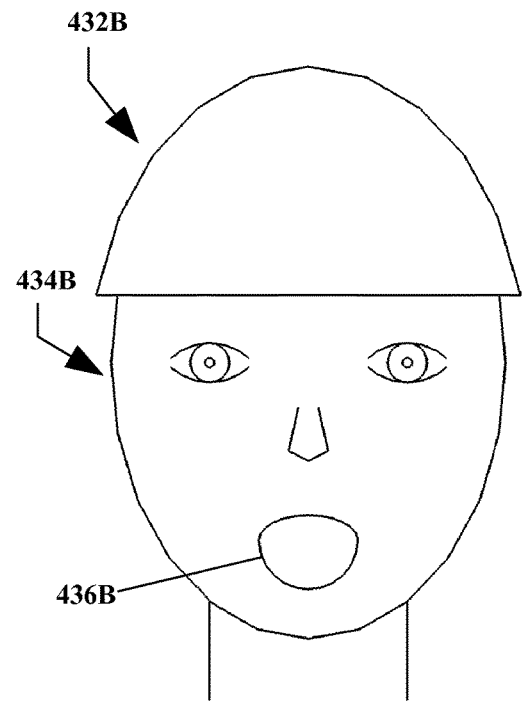
Figure 4C:
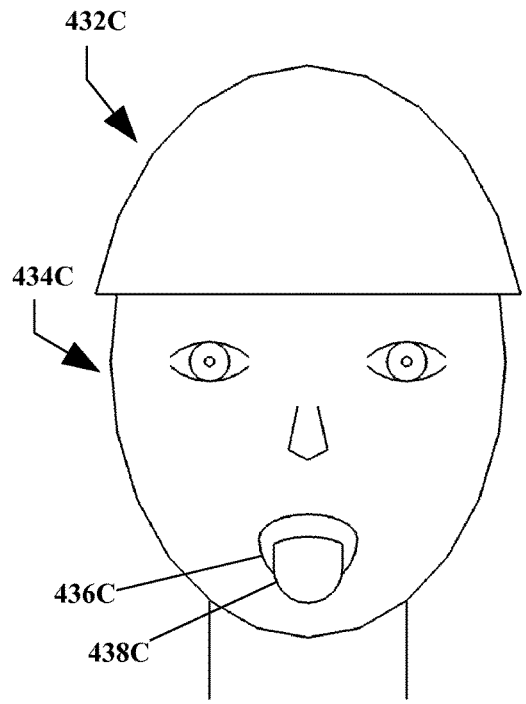
Figure 4D:
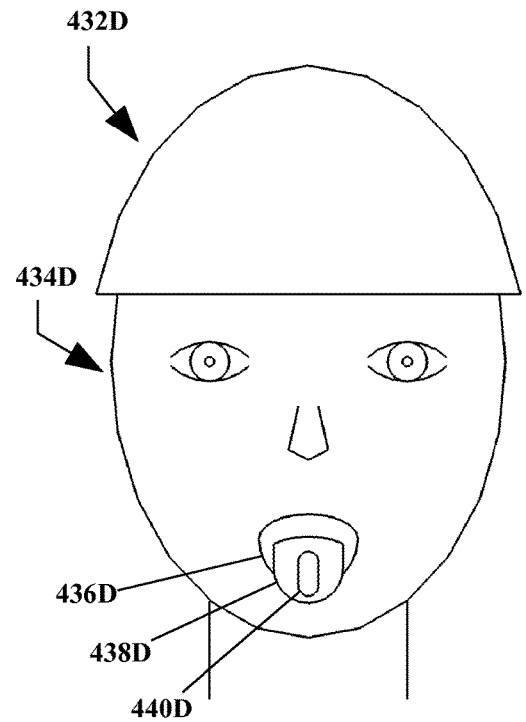

Now with regard to FIG. 4D, a subject 432D is shown, with the subject's face 434D visible, mouth 436D open, and tongue 438D extended. A medication 440D is also visible disposed on the tongue 438D, as may be done when the subject 432D is administering the medication 440D orally, with the medication 440D in the example of FIG. 4D being illustrated as an oblong tablet, capsule, etc.

In FIG. 4E, a subject 432E is again shown with the subject's face 434E visible, mouth 436E open, and tongue 438E extended, and with a medication 440E is disposed on the tongue 438E, e.g. for oral administration to the subject 432E. In addition, an electronic device 442E illustrated in the form of a smart phone is shown disposed proximate and in front of the face 434E of the subject 432E. (Typically a smart phone or similar electronic device 442E may be held by the subject 432E, for example in a hand, but for purposes of simplicity the hand is not shown herein.)

Figure 4E:
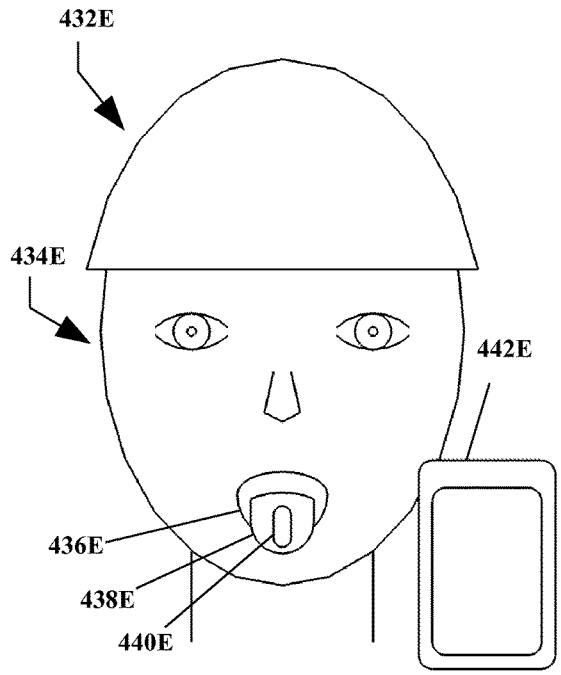
Figure 4F:
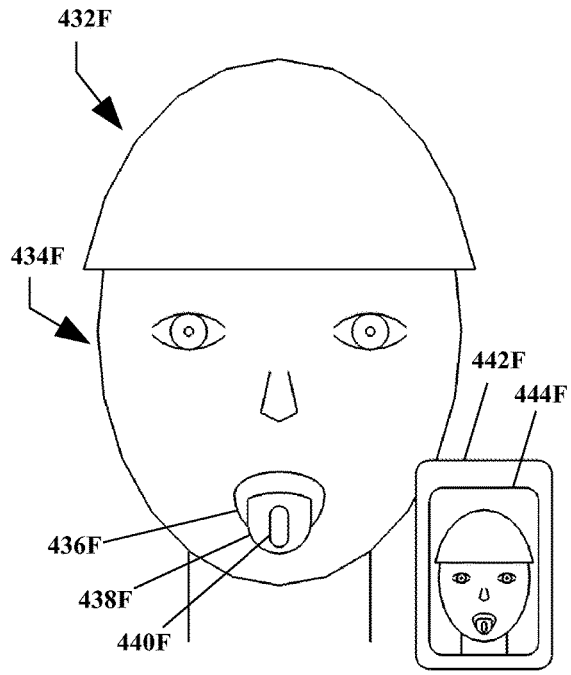

Turning to FIG. 4F, a subject 432F is shown with the face 434F visible, mouth 436F open, and tongue 438F extended, and with a medication 440F is disposed on the tongue 438F. An electronic device 442F also is shown. In addition, an image 444F of the subject 432F is shown displayed on the device 442F, as may be the case when such an image 444F is captured by the device 442F. A smart phone for example typically includes one or more digital cameras thereon, adapted for capturing images such as the image 444F shown in FIG. 4E Colloquially, when a subject 432F captures an image 444F of himself/herself using a device 442F such as a smart phone, the image 444F may at times be referred to as a "selfie". Thus it may be said that in FIG. 4F, the subject 432F may be seen to have captured a selfie 444F, while in the process of orally administering the medication 440F to himself/herself.

Figure 4G:
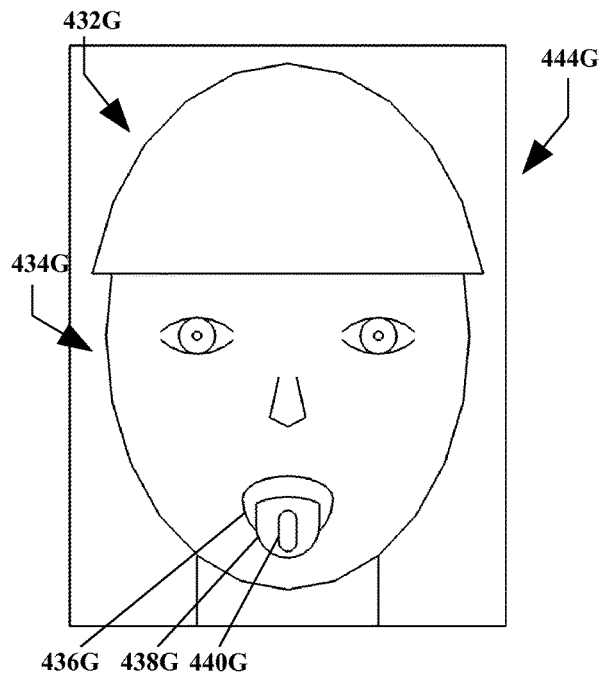

Now with reference to FIG. 4G, an image 444G is shown as may correspond to the image 444F shown captured in FIG. 4E As may be seen, the image 444G depicts therein a portion of the subject 432G, including the face 434G, the open mouth 436G, and the tongue 438G, with a medication 440G disposed on the tongue 438G. As noted with regard to FIG. 4F, such an image 444G may be referred to colloquially as a "selfie"; given that the image 444G shown in FIG. 4F more particularly shows the subject 432G administering a medication 440G, the image 444G may also reasonably be referred to as an "Rx selfie" (though the medication 440G is not necessarily limited to an "Rx" or prescription medication).

Thus, collectively FIG. 4A through FIG. 4G may be seen as a series of events relating to a subject administering an oral medication to himself/herself, and recording an image representative of that series of events, in the form of an "Rx selfie" showing the subject with medication disposed on his/her tongue, ready to be swallowed. It is noted that none of the events shown in FIG. 4A through FIG. 4G necessarily are themselves required for an embodiment of the present invention that (as in the example of FIG. 1) receives standards and makes comparisons with regard to a subject identity, therapeutic event, parameter, etc.; actually taking a medication (i.e. executing the therapeutic event) for example may not necessarily be part of a given embodiment of a method according to the present invention. However, an image such as the image 444G shown to have been captured in FIG. 4G may, for example, be received in a transmission such as the transmissions described previously with regard to FIG. 1 (e.g. in step 114 thereof) and elsewhere herein. Thus, the arrangements of FIG. 4A through FIG. 4G may be considered to illustrate the present invention, at least insofar as providing an example of information as may be received and considered by the present invention.

However, the present invention is not limited to or by the events shown in FIG. 4A through FIG. 4G. The present invention for example is not limited only to taking an oral medication or taking any medication as a therapeutic event, to a subject self-administering a medication or otherwise performing a therapeutic event himself/herself, to a subject recording the therapeutic event as shown, recording the therapeutic event himself/herself, recording the therapeutic event with a smart phone/other electronic device, using an image to record/represent the therapeutic event, etc. Although the "Rx selfie" as shown in FIG. 4A through FIG. 4G may represent one example of information as may be transmitted for use in the present invention, the present invention is not limited only thereto, and other arrangements may be equally suitable.

Figure 5:
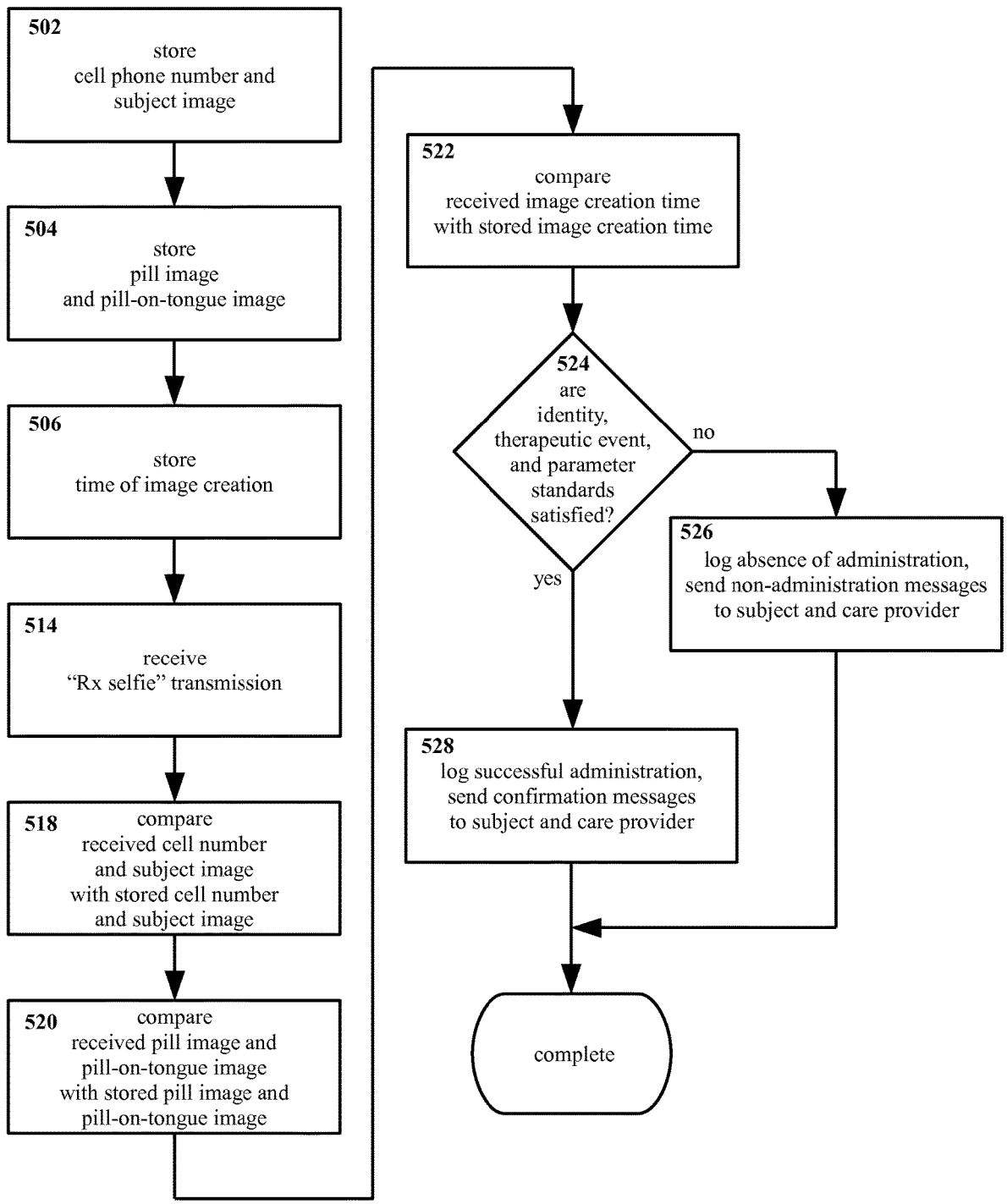
FIG. 5 shows another example embodiment of a method for verifying therapeutic compliance according to the present invention, as may be applicable to an approach utilizing an "Rx selfie" image.

However, the example having been presented in FIG. 4A through FIG. 4G, in FIG. 5 an example of a method according to the present invention is shown that is in at least some ways specific to the capture and transmission of an "Rx selfie" as already shown and described. Such a concrete example is presented as being illustrative, but the present invention is not limited only thereto, and other arrangements may be equally suitable.

In the arrangement of FIG. 5, a cell phone number and a subject image are stored 502, with the further requirement that a received cell phone number must match the stored cell phone number and a received subject image must substantially match the subject image. This collectively may be considered to represent a standard for verifying the subject's identity, i.e. a subject identity standard. For purposes of this example, the cell phone number and subject image may be considered to be stored in a central data store, such as a cloud storage. Likewise for purposes of this example, the subject may himself or herself enter or upload the cell phone number and subject image in establishing a user account. (These comments regarding storing and entering information also may apply to information in steps 504 and 506 below.) However, these are examples only, and other arrangements may be equally suitable.

A pill (medication) image and an image of a pill disposed on the subject's tongue also are stored 504, with the further requirement that a received medication image must substantially match the stored medication image and a received image of a pill disposed on the subject's tongue must substantially match the stored pill-on-tongue image. This collectively may be considered to represent a standard for verifying the execution of a therapeutic event, i.e. a therapeutic event standard.

A range of time of image creation is stored 506, with the further requirement that a received time of image creation must be within the stored image creation time range. This may be considered to represent a standard for verifying a parameter of a therapeutic event, i.e. a parameter standard. A range of time of image creation is stored 506, with the further requirement that a received time of image creation must be within the stored image creation time range. This may be considered to represent a standard for verifying a parameter of a therapeutic event, i.e. a parameter standard.

Still with reference to FIG. 5, an "Rx selfie" transmission is received 514. For purposes of this example, it may be considered that the "Rx selfie" is an attachment to a message sent from a smart phone through a cellular phone network to a processor that is in communication with the data store on which data stored in steps 502, 504, and 506.

It is noted that an arrangement wherein a determination is made as to whether a message is received as shown in FIG. 2 and elsewhere herein may be equally suitable, and/or other variations in method from what is shown in FIG. 5 likewise may be equally suitable. However for purposes of simplicity the example of FIG. 5 considers that a transmission is indeed received 514.

In step 518 the cell phone number of the received "Rx selfie" transmission (typically though not necessarily metadata of the transmission) is compared against the stored cell phone number, and the face in the "Rx selfie" image itself is compared against the stored subject image. For this example, it may be considered that cell phone number comparison is a numerical comparison (i.e. are the numbers the same?), and that the image comparison includes image recognition to determine whether the subject in the stored image is the same as the subject in the "Rx selfie". The comparison may also include options for addressing instances wherein (for example) the received image does not actually show a person's face. For example, it is at least in principle possible for a subject to believe that he or she has taken a suitable image, when in fact he or she has not.

In step 520 the pill in the "Rx selfie" is compared against the stored image of the pill, and the arrangement of the pill in the "Rx selfie" is compared against the stored image of the subject with the pill disposed on the subject's tongue. Also for this example, it may be considered that the pill image comparison includes object recognition to determine whether the pill in the "Rx selfie" is the same type of pill as in the stored pill image, and that the pill-on-tongue image comparison includes action recognition to determine whether the action depicted in the "Rx selfie" is the action of taking the medication as in the stored pill-on-tongue image. The comparison may also include options for addressing instances wherein (for example) the received image does not actually show a person's face.

It is noted that, as described with respect to steps 518 and 520, the single "Rx selfie" image may be used for multiple comparisons, e.g. face recognition, object recognition, action recognition, etc. Although this example is presented under the expectation that separate images may be used for the stored face image, stored pill image, etc. (e.g. to provide comprehensive or controlled image data for comparison), for certain embodiments one stored image likewise may be used for multiple comparisons. Conversely, the use of multiple received images and/or multiple stored images for each comparison likewise may be suitable (e.g. front and profile images of the subject for subject image comparison).

Continuing in FIG. 5, in step 522 the image creation time for the "Rx selfie" is compared with the stored time range. It may be considered that the image creation time comparison is a numerical comparison, i.e. does the creation time for the "Rx selfie" fall numerically within the numerical limits of the stored time range? The comparison may also include options for addressing instances wherein (for example) the received image does not show a valid creation time, shows a technically valid but unlikely creation time (e.g. a digital image with a creation time of Jan. 1, 1900), etc.

A determination is made 524 as to whether the subject identity standard, therapeutic event standard, and parameter standards (as established in steps 502, 504, and 506) are satisfied (considering the comparisons made in steps 518, 520, and 522).

If the determination 524 is positive the method continues with step 528 wherein the successful administration of the medication is logged (i.e. stored within the data store) along with the received "Rx selfie" transmission itself, a confirmation message indicating successful administration and logging is sent back to the subject, and a similar confirmation message indicating successful administration and logging is sent to a physician or other health care provider for the subject.

If the determination 524 is negative the method continues with step 526 wherein the absence of evidence of successful administration of the medication is logged (i.e. stored within the data store), a failure message is sent to the subject indicating that administration of the medication was not recorded and/or is presumed not to have taken place, and a similar failure message is sent to a physician or other health care provider for the subject.

Following either step 528 or step 526 the method is complete.

As already noted, it is emphasized the "Rx selfie" arrangement in FIG. 5 is an example only, and the present invention is not limited only thereto.

Figure 6:
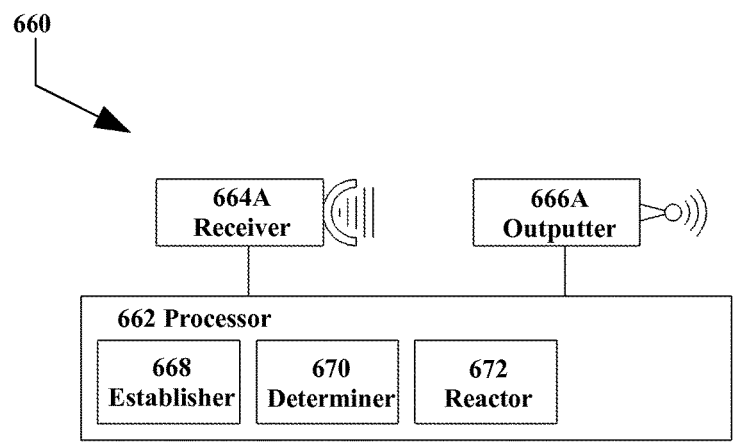
FIG. 6 shows an example embodiment of an apparatus for verifying therapeutic compliance according to the present invention, in schematic form.

Now with reference to FIG. 6, therein an example embodiment of an apparatus according to the present invention is shown in schematic form.

As shown in FIG. 6, the example apparatus 660 includes a processor 662 adapted to execute executable instructions thereon. The invention is not particularly limited with regard to the choice of processor 662. Suitable data processors 662 include but are not limited to digital electronic microprocessors. Although the processor 662 may be referred to in at least some places herein as a self-contained physical device for purposes of clarity, this is not required, and other arrangements may be suitable. For example, the processor 662 may constitute two or more physical processors working cooperatively, a processing capability in a network without a well-defined physical form, etc.

The apparatus 660 also includes a receiver 664 in communication with the processor. The receiver 664 is adapted to accept input for the processor 662, including but not limited to transmissions as described previously herein. The receiver 664 also may be adapted to receive other input, including but not limited to subject identity standards, therapeutic event standards, and parameter standards as described previously herein.

The present invention is not particularly limited with regard to the choice of receiver 664. As shown in FIG. 6 the receiver 664 is illustrated as a wireless receiver, for example a wifi or Bluetooth receiver, but this is an example only. Other approaches for receiving input, including but not limited to wired communication, may be equally suitable.

The apparatus 660 further includes an outputter 666 in communication with the processor. The outputter 666 is adapted to deliver output from the processor 666, including but not limited to satisfaction reactions. The outputter also may be adapted to deliver other output from the processor 662, including but not limited to non-satisfaction reactions.

A number of elements are instantiated on the processor 662, namely an establisher 668, a determiner 670, and a reactor 672. For at least certain embodiments the establisher 668, determiner 670, and reactor 672 may be entirely composed of executable instructions and/or data, for example in the form of software, but the present invention is not limited only thereto. Forms of establisher 668, determiner 670, and reactor 672 that are partially or entirely hardware may be equally suitable. In addition, although the establisher 668, determiner 670, and reactor 672 are shown as distinct elements, the establisher 668, determiner 670, and reactor 672 may be integrated together (e.g. as a unified program) or further subdivided (e.g. as collections of files, subroutines, etc.).

The establisher 668 is adapted to establish an identity standard, a therapeutic event standard, and a parameter standard. Identity standards, therapeutic event standards, parameter standards, and establishment thereof have been described previously herein. The establisher 668 may communicate with and/or operate in cooperation with the receiver 664, for example establishing an identity standard, therapeutic event standard, and/or parameter standard utilizing data received via the receiver 664, or even in some embodiments acquiring an identity standard, therapeutic event standard, and/or parameter standard entirely from the receiver 664.

The determiner 670 is adapted to make a determination as to whether a transmission, for example as received by the receiver 664, satisfies an identity standard, therapeutic event standard, and/or parameter standard (for example as established by the establisher 668). As already described, determination may include therein various comparisons, analyses, etc. of the transmission, and the determiner 670 may carry out such actions in part or in full.

The reactor 672 is adapted to execute a satisfaction reaction. Satisfaction reactions have been described previously herein. The reactor 672 may communicate with and/or operate in cooperation with the outputter 666, for example using the outputter 666 to send a satisfaction response as part of a satisfaction reaction. The reactor 672 may also carry out other functions including but not limited to executing non-satisfaction reactions.

Figure 7:
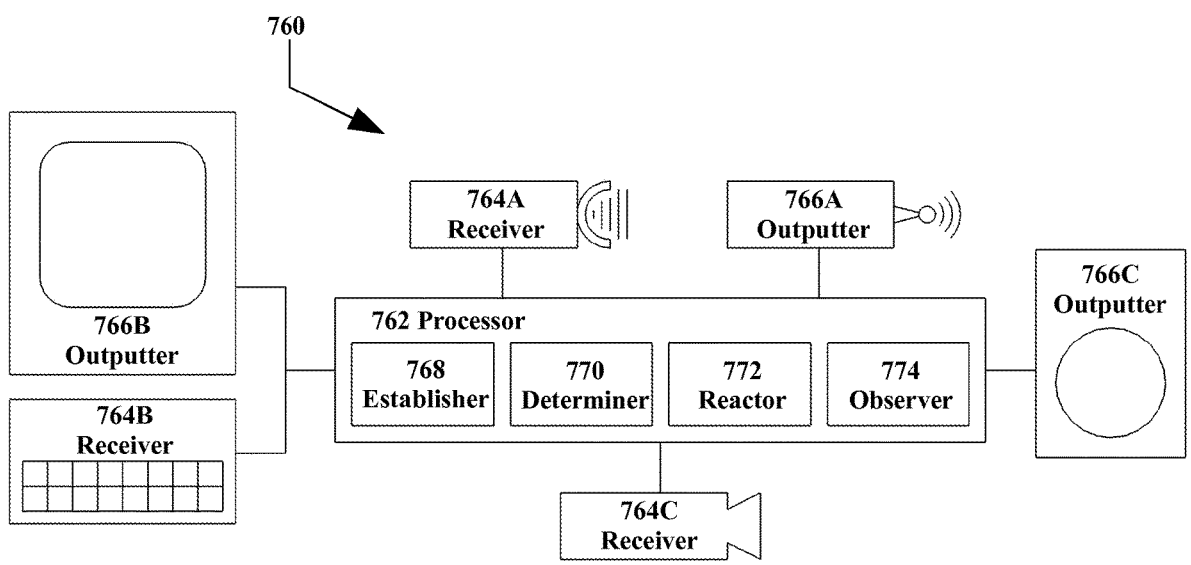
FIG. 7 shows an example embodiment of an apparatus for verifying therapeutic compliance according to the present invention, showing additional optional elements, in schematic form.

Many variations in terms of elements and functions thereof may be possible within the present invention. With reference now to FIG. 7, certain variations—though by no means the only variations within the scope of the present invention—are shown for an apparatus according to the present invention.

As shown in FIG. 7, the example apparatus 760 therein includes a processor 762, and a receiver 764A and outputter 766A in communication therewith. As in FIG. 6, the receiver 764A and outputter 766A are illustrated as wireless devices, adapted to receive and output information through wifi, Bluetooth, etc.

However, as has been noted such arrangements for receivers and outputters are examples only, and other arrangements may be equally suitable. For example, as shown in FIG. 7 the apparatus 760 therein also includes receivers 764B and 764C, in the forms of a keypad and an imaging sensor respectively. With such an arrangement, a transmission may be received from the receiver 764C in the form of one or more images captured thereby. Similarly, some or all of the identity standard, therapeutic event standard, and/or parameter standard may be established via the receiver 764C in the form of one or more images captured thereby. Alternately, some or all of the identity standard, therapeutic event standard, and/or parameter standard may be established via the receiver 764B in the form of data keyed in therewith. Other arrangements also may be equally suitable.

The apparatus 760 also includes outputters 766B and 766C in the forms of a display screen and a data store such as a hard drive or solid state drive, respectively. With such an arrangement, a satisfaction reaction (and/or a non-satisfaction reaction) may be executed in storing information in the outputter 766C. Similarly, some or all of a satisfaction (and/or a non-satisfaction reaction) may be executed in displaying information with the outputter 766B.

The present invention is not limited only to the receivers 766A, 766B, and 766C as shown, nor to only the outputters 768A, 768B, and 768C as shown. In addition, a single element may serve as both inputter and outputter, for example a data store may both convey information to the processor 762 and convey information from the processor 762 within a single apparatus 760. Likewise, a touch screen may serve as both receiver and outputter, etc.

It is noted that a receiver is not required to receive information from outside of whatever physical device (if any) that incorporates the processor (though such function also is not prohibited). Rather, the receiver serves to receive information that is then passed along to the processor. Thus a data store or other element within the same physical device as the processor or otherwise in communication therewith also may serve as a receiver, since the processor may receive data therefrom. Similarly, an outputter is not required to output information outside of whatever physical device (if any) that incorporates the processor (though again such function is not prohibited). Rather, the outputter serves to convey information from the processor, in similar fashion to the receiver conveying information to the processor.

Still with reference to FIG. 7, therein an establisher 768, determiner 770, and reactor 772 are shown instantiated on the processor 762 as has been described (for example with regard to FIG. 6). However, the present invention is not limited only to an establisher 768, a determiner 770, and a reactor 772. For example, as may be seen in FIG. 7 an observer 774 also is instantiated on the processor 774.

The observer 774 is adapted to observe a presence of a transmission. That is, as has been described previously herein, it is not necessary to assume the receipt of a transmission, but rather the presence or absence of a transmission in itself may be considered according to the present invention, for example in sending a non-satisfaction reaction if no transmission is received (rather than only if a transmission is received but is unsatisfactory). The observer 774 may include executable instructions, and may be composed entirely of executable instructions, data, etc., though the observer also may be composed partially or entirely of hardware, etc. in other embodiments.

Other elements likewise may be disposed on the processor 762, and/or placed in communication therewith.

The present invention may be disposed on and/or incorporated into a wide variety of forms. For example, an apparatus similar to that in FIG. 7 may be implemented with a smart phone, the smart phone having executable instructions (e.g. a program) instantiated on the processor thereof. Smart phones and/or other portable electronic devices may exist or at least may be produced according to the present invention having processors at least analogous to the processor 762 in FIG. 7, receivers (e.g. cellular network receivers, touch screens, cameras) at least analogous to the receivers 764A, 764B, and 764C in FIG. 7, and outputters (e.g. cellular network transmitters, display screens, hard drives or solid state drives) at least analogous to the outputters 766A, 766B, and 766C in FIG. 7. With a suitable establisher 768, determiner 770, reactor 770, etc. instantiated thereon a smart phone may be made to serve as an apparatus according to the present invention, and/or carry out a method according to the present invention.

As a more concrete example, a smart phone (with suitable executable instructions disposed thereon) may enable a subject to enter an identity standard, therapeutic event standard, and parameter standard, those standards then being established onto the processor thereof. The subject may then take an "Rx selfie" which is received by the smart phone's processor. Comparisons and determinations may likewise be carried out in the smart phones processor, with satisfaction and/or non-satisfaction reactions also carried out by the smart phone's processor, possibly with a satisfaction/non-satisfaction response displayed on the smart phone screen (and/or sent to other entities).

In such instance, a subject may perform the entirety of a method according to the present invention using an integrated portable device. However, this is an example only and other arrangements may be equally suitable. For example, an apparatus according to the present invention may be a desktop device.

In addition, an apparatus according to the present invention may be disposed as (and/or a method according to the present invention carried out by) a distributed device. As a more concrete example, and to continue reference to the example of a smart phone above, a smart phone may serve to enable a subject to enter an identity standard, therapeutic event standard, and parameter standard and then send those standards on some remote processor (e.g. by communicating the standards thereto through the cellular network), where the standards are established on that processor. The subject may then transmit an "Rx selfie" or other information, which is received at the remote processor. Comparisons and determinations may likewise be carried out at the remote processor, with satisfaction and/or non-satisfaction reactions also carried out by the remote processor, possibly with a satisfaction/non-satisfaction response sent back to the subject (and/or to other entities).

At this point some discussion of advantages of the present invention may be illuminating.

Numerous medications and other therapeutic options exist. However, in many cases the effectiveness, and in some cases the safety, of medications and/or other therapeutic events may depend strongly on factors such as how, when, and/or under what circumstances the relevant therapeutic events are carried out.

For example, certain medications for treating high blood pressure may be most effective if a relatively stable level of medication is maintained in the blood stream. However, not all patients respond equally to all medications, nor do all patients respond equally to changes in dose of a given medication. In order for a medical professional to determine the effectiveness of a drug regime in a particular patient, for example, it may be useful for the medical professional to know, preferably with high precision and high confidence, if the medication was taken, when the medication was taken, under what circumstances the medication was taken, etc.

The present invention enables the collection of information on such matters.

For example, to contine the earlier example of an "Rx selfie", if a subject captures an image of himself or herself taking a medication each time the medication is taken, this may provide a log of data that may be useful to a physician treating the subject. Such a log, including as noted images of the subject with (for example) pills on his or her tongue, may be treated as a high-confidence record that medication is being taken. If the log also includes information regarding when the medication was taken (such as a creation time for the images), the log also may be treated as a high-precision record of when the medication is taken.

Such a log may not be sufficient to entirely eliminate the possibility of deliberate deception; it may be possible in principle to deliberately mislead a physician even with such a log by placing a pill on ones tongue, sending an "Rx selfie", and then spitting out the pill. However, for many therapeutic events deliberate fraud may be of less concern than accidental failure. For example, a patient taking glaucoma medication may be considered unlikely to deliberately stage false instances of taking a medication, given that failure to take the medication may result in permanent and severe vision damage.

However, simply forgetting to take glaucoma medication, or any of a number of other medications, may be another matter. While a subject may forget to take an "Rx selfie", if such an image is taken then the image very likely represents an actual incident of taking a medication. In addition, while forgetting to take a medication is certainly possible, forgetting to take an "Rx selfie" while taking a medication may be less likely; the subject is, after all, taking the medication, so remembering to take an image (at least once taking such an image becomes habit) may be unlikely. In addition, persons with smart phones frequently carry them as a matter of course, so it may be considered unlikely that a subject would not have his or her smart phone available. Thus, absence of an "Rx selfie" conversely may be considered reliable evidence that the medication was not taken. Even if potentially imperfect, validating compliance with prescribed therapeutic events according to the present invention may at least arguably be more effective than certain conventional approaches, such as written logs, personal memory recall, and so forth.

Even if compliance with a prescribed therapeutic event is imperfect, knowledge of the imperfection may nevertheless be medically useful. For example, knowing that a particular patient has missed 5% of medication doses in the morning but 15% in the evening may suggest that a once-a-day medication may be more effective than a twice-a-day medication for that patient. Likewise, merely being aware that a patient has missed for example 20% of medication doses in the past week may help a physician or other health care professional determine whether the observed or reported response of the patient to a medication (for better or worse) and/or observed or reported side effects are due to the medication or not, whether the medication is working at all, whether a different medication may be more useful, etc.

In addition, such information may be particularly useful in circumstances wherein the effectiveness of a particular therapeutic tool is unknown or uncertain, such as trials of drug efficacy, side effects, person-to-person variation, and so forth. In determining such factors, relatively small variations in how, when, if, etc. a drug is taken potentially may have significant effects on the results of the study (and may in some cases distort the apparent safety and effectiveness of the therapy in question). While approaches exist to compensate for lack of precision and/or lack of confidence in when, how, if, etc. a therapy is being carried out while studying that therapy, typically such approaches depend either on increasing sample sizes (i.e. more participants in the study), increasing study duration, and/or repetition of studies. It will be understood that larger, longer, and/or more studies may increase the cost of research, and/or may increase the time required for research. This in turn may increase the time and cost needed to develop a new drug or other therapy, and thus potentially may decrease the number of such therapies available and/or delay the available of such therapies.

Although the preceding examples are presented to illustrate potential advantages of the present invention, it is emphasized that the present invention is not limited thereto, and that other arrangements may be equally suitable.

Figure 8:
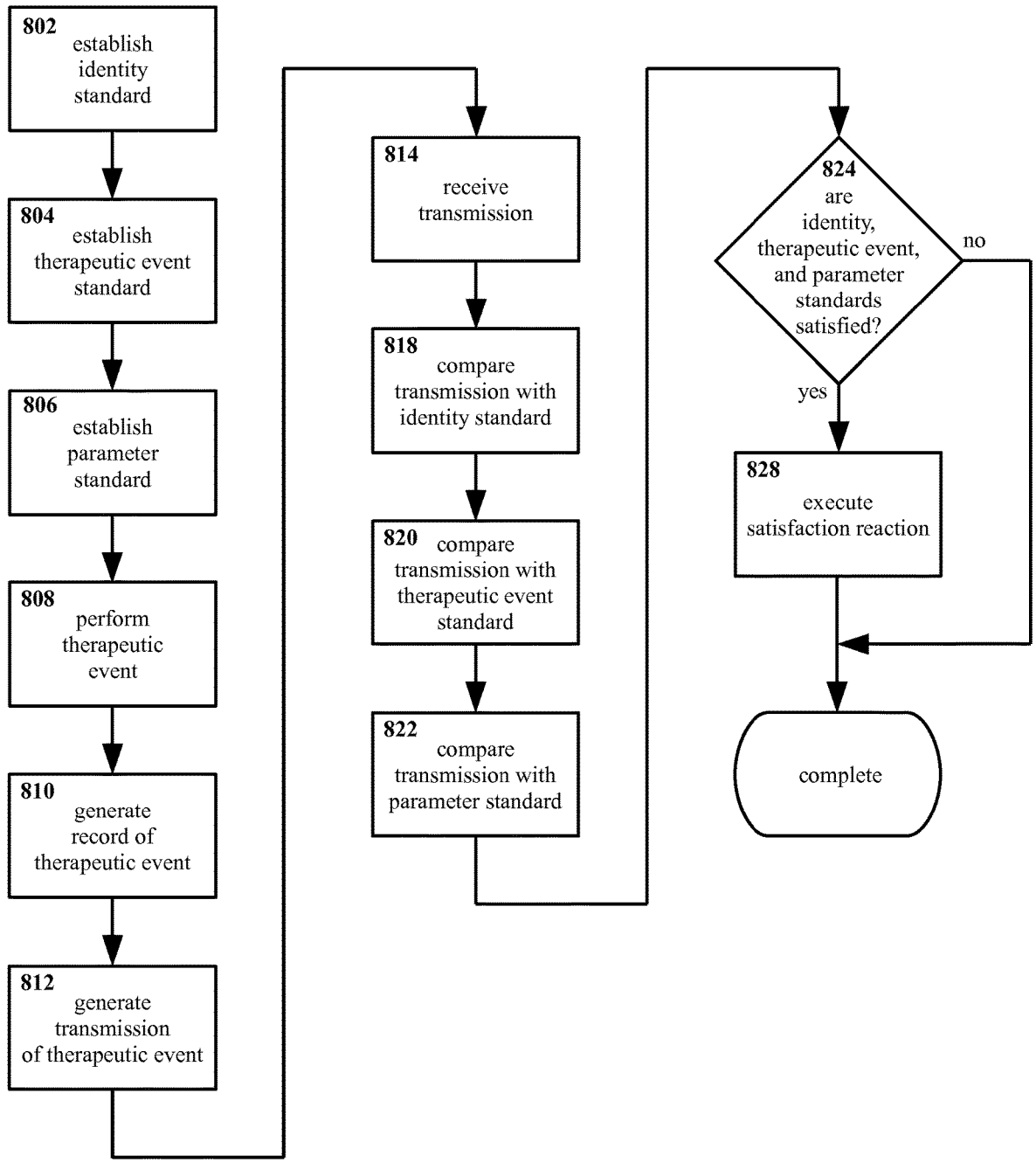
FIG. 8 shows an example embodiment of a method for verifying therapeutic compliance according to the present invention, with reference to certain user actions therein.

Now with reference to FIG. 8, therein is shown an example method according to the present invention wherein certain implicit events are shown as explicit, and at least potentially part of certain embodiments of the present invention.

In the example of FIG. 8, an identity standard is established 802, a therapeutic event standard is established 804, and a parameter standard is established 806.

Continuing in FIG. 8, a therapeutic event is performed 808, such as a person taking a medication. A record of the therapeutic event is generated 810, for example a "selfie" image of the person taking the medication, e.g. as taken with a cell phone or other device. A transmission is generated 812 such as a text, video, image, or e-mail message, e.g. as sent by a cell phone or other device.

As may be observed through consideration of previous illustrations and examples herein, such as FIG. 1 through FIG. 3 and FIG. 5, steps 808, 810, and/or 812 may not necessarily be present in all embodiments of the present invention. Steps 808, 810, and 812 in the example of FIG.

8 refer to actions taken and/or instigated by a user, such as taking an image with a cell phone camera, etc. For at least certain embodiments such actions may be, and/or may be considered to be, part of a method according to the present invention. However, this does not imply that a user himself or herself necessarily is part of the present invention. Likewise, steps such as 808, 810, 812 and/or similar events, while permissible for at least some embodiments of the present invention, are not required thereby. Furthermore, even where one or more of steps such as 808, 810, and 812 are included in an embodiment of the present invention, it is not required that all such steps be included.

Continuing in FIG. 8, the transmission is received 814. The transmission is compared with the identity standard 818, compared with the therapeutic event standard 820, and compared with the parameter standard 822. A determination is made 824 as to whether the identity standard, therapeutic event standard, and parameter standards are satisfied by the transmission.

If the identity standard, therapeutic event standard, and parameter standards are satisfied by the transmission, then the method continues with executing a satisfaction reaction 828, otherwise step 828 is skipped.

It is noted that an approach such as that shown in FIG. 8 (as well as other figures herein) may take various practical forms. For example, steps may be performed variously by one or more devices and/or systems, and/or one or more persons. As a more concrete example, steps 802, 804, and 806 may be performed within a portable electronic device such as a smart phone, through executable instructions instantiated on a processor therein. A subject may then perform the therapeutic event 808 on himself or herself (e.g. taking a medication), generate the record 810 thereof with the smart phone (for example by taking a picture with a camera therein), and generate the transmission 812 as a picture message, and send that message to some external system. That other system, for example a computer at a medical or research facility, may receive the transmission 814, compare the transmission with the identity standard 818, therapeutic event standard 820, and parameter standard 822, and make the determination 824. The medical/research computer then may also execute the satisfaction reaction 828 (or a non-satisfaction reaction, for embodiments that include such).

Alternately, steps 814 through 822 may be performed within the smart phone itself, without necessarily communicating with an external medical/research computer. In such instance the transmission may be considered to be sent to the smart phone itself, e.g. sent to some program, stored as data, etc., with the processor of the smart phone then carrying out comparisons, determinations, etc. for steps 818 through 828.

As yet another alternative, one person may perform the therapeutic event 808 in the form of taking (or being given) a medication, while another person uses a smart phone to generate a record 810 thereof and send a transmission to some recipient (whether the smart phone, a different smart phone, another person, a medical/research computer, etc.). Such an arrangement may be useful for example when the person receiving the medication (or otherwise the subject of the therapeutic event) is in the care of the person generating the record of the therapeutic event, such as a child in the care of a parent, a hospital patient in the care of medical personnel, etc. However, other arrangements also may be suitable.

The above are examples only. Although presented as concrete examples referring to physical devices (e.g. a smart phone), specific individuals (persons taking medication), etc., so as to illustrate possible implementations with regard to persons and devices for purposes of clarity, other arrangements may be equally suitable. The present invention is not limited only to smart phones, or to the "division of labor" referred to in the above examples with regard to persons and systems.

Now with reference to FIG. 9A through FIG. 9D, as described previously with regard to certain examples herein (such as FIG. 4A through FIG. 4G), certain embodiments of the present invention may make use of portable electronic devices such as a smart phone. However, as also noted the use of a smart phone is an example only. FIG. 9A through FIG. 9DF show another arrangement, utilizing a wearable electronic device worn on the wrist of a user. It is emphasized that the arrangement of FIG. 9A through FIG. 9D also is an example only; the present invention is not limited only to smart phones and/or wrist mounted devices. Other portable electronic devices, including but not limited to head mounted devices ("smart glasses"), may be equally suitable. Furthermore, the description of mobile devices is itself an example only, and other arrangements unrelated to mobile devices also may be equally suitable.

Figure 9A:
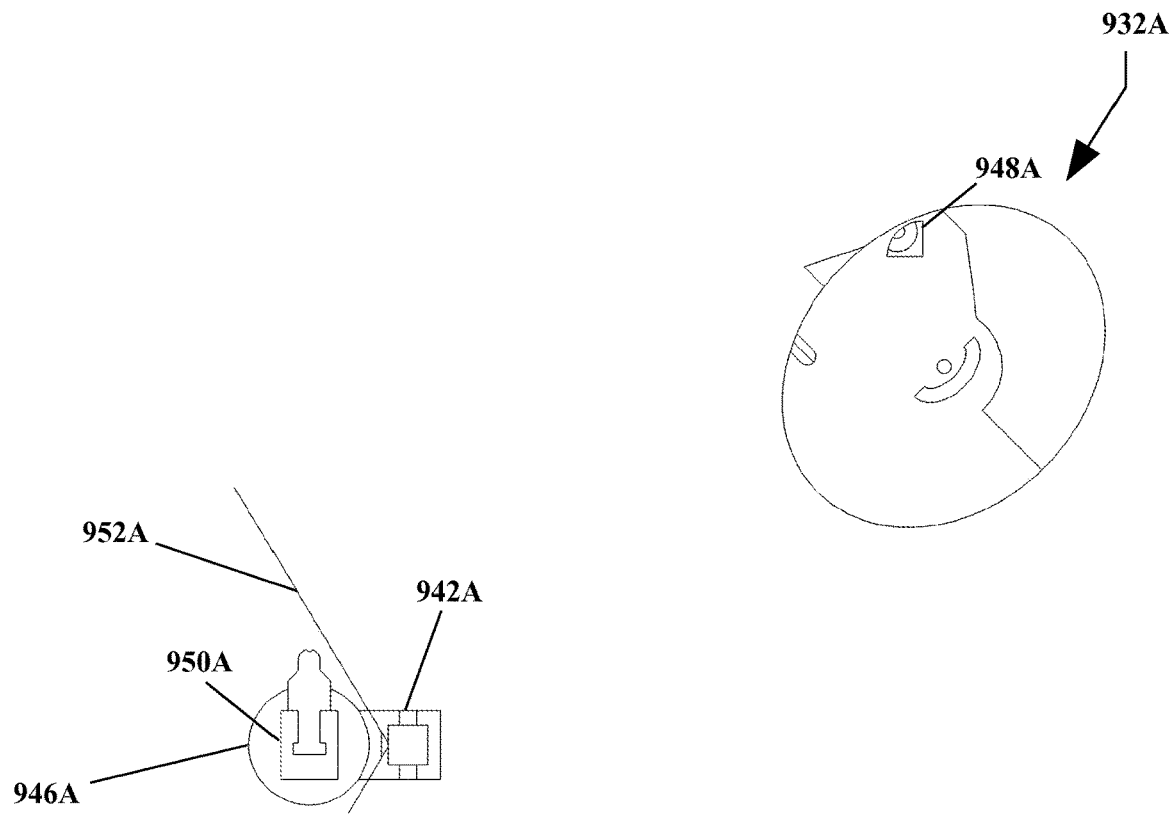
FIG. 9A through FIG. 9D show a sequence of events as may be associated with another example embodiment of a method for verifying therapeutic compliance according to the present invention, utilizing a wrist mounted portable electronic device.

With reference specifically to FIG. 9A, therein a subject 932A is shown. A hand 946A and an eye 948A of the subject 932A also are visible in FIG. 9A. It is emphasized that the subject 932A is not necessarily part of the invention, rather the subject 932A is shown here for explanatory purposes.

As may be seen, a container 950A of medication is disposed within the hand 946A of the subject 932A. FIG. 9A may be understood as showing an initial arrangement for dispensing a medication in the form of an eyedrop to the subject 932A.

In addition, the subject 932A in FIG. 9A wears on his/her hand 946A (more technically the wrist thereof) a wearable electronic device 942A such as a so-called smart watch. As may be seen, the wearable electronic device 942A includes therein an imager with a field of view 952A marked in FIG. 9A by lines, the field of view 952A encompassing at least some portion of the hand 946A. Depending on the orientation of the wearable electronic device 942A, the imager thereof, the posture of the hand 946A, etc., the field of view 952A may encompass varying portions of the hand 946A, entities disposed therein, etc. The present invention is not limited with regard to how the wearable electronic device 942A is worn, and/or what field of view 952A may be exhibited thereby.

However, for at least certain embodiments of the present invention is may be useful to configure a wearable electronic device 942A such as that shown in FIG. 9A so that an imager thereof is on the palmward side (i.e. the "inside") of the wrist. More particularly, an arrangement such that the field of view 952A of the imager encompasses at least a portion of the palm. Typically though not necessarily, this may be accomplished through disposing an imager on the palmward side of the wrist.

At least certain advantages may follow for such an arrangement wherein at least a portion of the palm is disposed within the field of view 952A, including but not limited to the following. Manipulation of objects typically may be accomplished on the palm side thereof. That is, objects may be gripped in the palm, or at least held on the palm side of the hand. Similarly, keystrokes may be delivered from the palm side of the fingertips, e.g. with fingers partially bent so as to extend past the palm. Furthermore, objects that may not be directly manipulated but that may nevertheless be of interest regarding manipulation also may be proximate the palm. For example, even if a plate is never held, nor the contents thereof directly picked up, that plate, the contents of that plate, the implements (if any) used to manipulate the plate (e.g. knife, fork, spoon, chopsticks, etc.) nevertheless may be in proximity to and/or facing the palms at least intermittently. Thus, by disposing a field of view 952A so as to view some or all of the palm and/or some portion of space proximate thereto, images (and/or other sensory data; the present invention is not limited only to imagers as sensors or sources of sensory data) of a hand, fingers, objects (and/or other entities) held, objects manipulated, nearby objects, etc. may be obtained.

However, the use of an imager disposed on the inside of the wrist so as to exhibit a field of view 952A encompassing some or all of the palm and/or regions proximate thereto is an example only, and other arrangements may be equally suitable.

Figure 9B:
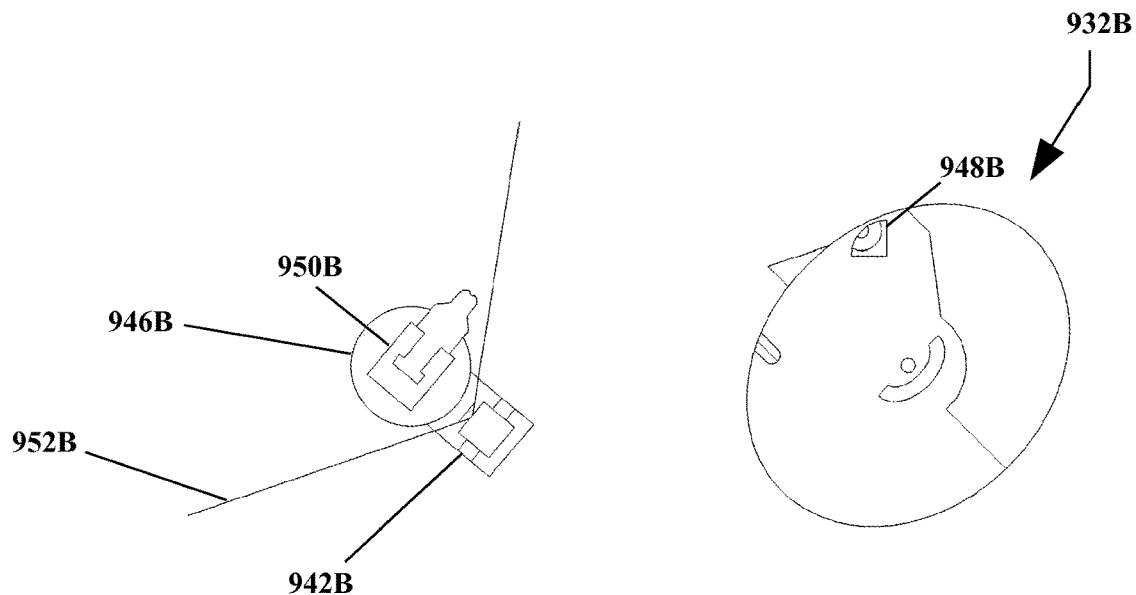
Figure 9C:
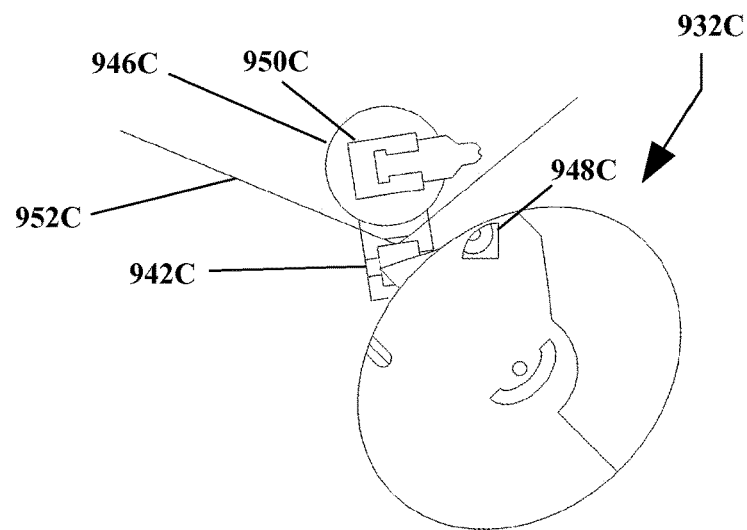
Figure 9D:
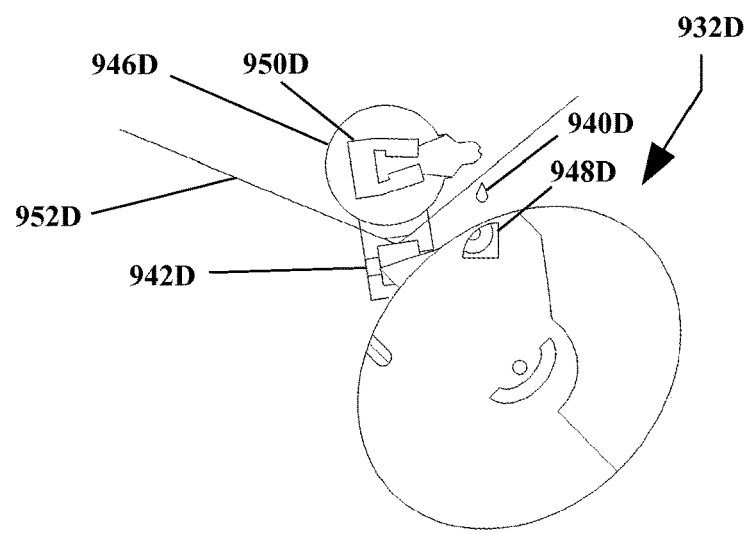

Still with reference to FIG. 9A, although a field of view 952A is shown therein it is not implied that an image is or must be obtained in the configuration shown. Although an image (e.g. as may satisfy an identity, therapeutic, and/or parameter standard) may be obtained in the configuration shown in FIG. 9A, or at any other configuration as shown in FIG. 9B through FIG. 9D or some other configuration and/or time, no particular time or configuration is necessarily required for obtaining such an image. Images and/or other data, where obtained, may be obtained at any point or points throughout the arrangement of FIG. 9A through FIG. 9D, depending on the particulars of a given embodiment.

With regard to the particular configuration of FIG. 9A, the medication container 950A as well as at least a portion of the hand 946A is within the field of view 952A, and thus if an image were taken by the imager of the wearable electronic device 942A the medication container 950A and at least a portion of the hand 946A may be visible in such an image.

Now with reference to FIG. 9B, therein is again visible a subject 932B, a hand 946B and eye 948B thereof, a medication container 950B disposed in the hand 946B, and a wearable electronic device 942B disposed on the hand 946B. As may be seen through comparison with FIG. 9A the hand 946B has been raised partway toward the eye 948B, as may be the case for a motion to administer an eyedrop medication. As in FIG. 9A the medication container 950B as well as at least a portion of the hand 946B is within the field of view 952B.

Referring to FIG. 9C, again a subject subject 932C, a hand 946C and eye 948C thereof, a medication container 950C disposed in the hand 946C, and a wearable electronic device 942C disposed on the hand 946C. In FIG. 9C the hand 946C has been raised to a position above the eye 948C, as for administering an eyedrop medication. The medication container 950C and at least a portion of the hand 946C is within the field of view 952C.

Turning now to FIG. 9D, a subject subject 932D, a hand 946D and eye 948D thereof, a medication container 950D disposed in the hand 946D, and a wearable electronic device 942D disposed on the hand 946D. In FIG. 9D the hand 946D has squeezed the medication container 950D so as to release a drop of medication 940D from a position above the eye 948D. Administering an eyedrop in such fashion may constitute a therapeutic event, for at least certain embodiments of the present invention.

The medication container 950D and at least a portion of the hand 946D is within the field of view 952D. The medication 940D itself is not within the field of view 952D as shown. However, given the arrangement of the medication container 950D it may be that at some point prior to the arrangement depicted in FIG. 9D the medication 940D may have been within the field of view 952D. Nevertheless, the present invention does not necessarily require that either a medication (for arrangements wherein a therapeutic event is related to a medication) or any other particular entity necessarily must be within the field of view of a sensor, or present within a transmission, except as otherwise specifically indicated herein. An arrangement wherein an image is taken at a moment corresponding to FIG. 9D, wherein the medication 940D is not visible, may be suitable.

As previously noted, the present invention does not require an image (or other data) be acquired at any particular time. Typically, though not necessarily, for an example arrangement wherein a medication is being dispensed as a therapeutic event an image (or other data) including the medication therein may be suitable, but an image showing a container held in hand, being moved upward, etc. also may be suitable.

In addition, it is emphasized that collecting data, generating images, etc. is not necessarily required to be a conscious or deliberate event insofar as the subject is concerned. The image may be obtained automatically, for example triggered based on sensor input (image evaluation, accelerometers and/or gyroscopes within the wearable electronic device, compression sensors within the medication container, etc.) as may indicate a medication being dispensed. Images also may be obtained at intervals regardless of sensor input or other factors, and evaluated to determine whether a therapeutic event of interest is evidenced by those images. Other arrangements also may be equally suitable. In addition, although deliberate action on the part of a subject or some other entity is not required for the present invention, such deliberate action also is not necessarily excluded.

Although not necessarily the case in the particular example of FIG. 9A through FIG. 9D, an imager in a wearable electronic device may include, at least intermittently, the face of the subject within the field of view thereof. This may depend on factors such as the field of view of the imager, the arrangement of the wearable electronic device, the anticipated motion(s) associated with a therapeutic event, etc.

Figure 10:
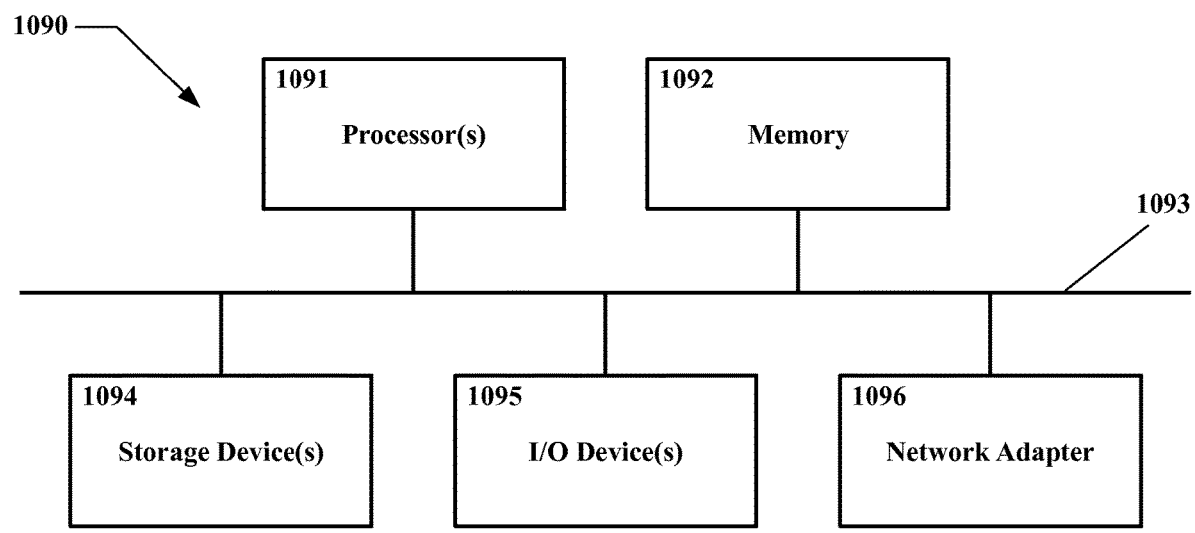
FIG. 10 shows a block diagram of a processing system that may implement operations of the present invention.

Now with reference to FIG. 10, a block diagram is shown therein of an apparatus that may perform various operations, and store various information generated and/or used by such operations, according to an embodiment of the disclosed technique. The apparatus may represent any computer or processing system described herein. The processing system 1090 is a hardware device on which any of the other entities, components, or services depicted in the examples of FIG. 1 through FIG. 8 (and any other components described in this specification) may be implemented. The processing system 1090 includes one or more processors 1091 and memory 1092 coupled to an interconnect 1093. The interconnect 1093 is shown in FIG. 9 as an abstraction that represents any one or more separate physical buses, point to point connections, or both connected by appropriate bridges, adapters, or controllers. The interconnect 1093, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire".

The processor(s) 1091 is/are the central processing unit of the processing system 1090 and, thus, control the overall operation of the processing system 1090. In certain embodiments, the processor(s) 1091 accomplish this by executing software or firmware stored in memory 1092. The processor(s) 1091 may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices.

The memory 1092 is or includes the main memory of the processing system 1090. The memory 1092 represents any form of random access memory (RAM), read-only memory (ROM), flash memory, or the like, or a combination of such devices. In use, the memory 1092 may contain a code. In one embodiment, the code includes a general programming module configured to recognize the general-purpose program received via the computer bus interface, and prepare the general-purpose program for execution at the processor. In another embodiment, the general programming module may be implemented using hardware circuitry such as ASICs, PLDs, or field-programmable gate arrays (FPGAs).

The network storage adapter 1094, a storage device(s) 1095, and I/O device(s) 1096, are also connected to the processor(s) 1091 through the interconnect 1093 The network adapter 1094 provides the processing system 1090 with the ability to communicate with remote devices over a network and may be, for example, an Ethernet adapter or Fibre Channel adapter. The network adapter 1094 may also provide the processing system 1090 with the ability to communicate with other computers within the cluster. In some embodiments, the processing system 1090 may use more than one network adapter to deal with the communications within and outside of the cluster separately.

The I/O device(s) 1096 can include, for example, a keyboard, a mouse or other pointing device, disk drives, printers, a scanner, and other input and/or output devices, including a display device. The I/O device(s) 1096 also may include, for example, cameras and/or other imagers adapted to accept visual input including but not limited to postures and/or gestures. The display device may include, for example, a cathode ray tube (CRT), liquid crystal display (LCD), or some other applicable known or convenient display device. The display device may take various forms, including but not limited to stereo displays suited for use in near-eye applications such as head mounted displays or other wearable devices.

The code stored in memory 1092 may be implemented as software and/or firmware to program the processor(s) 1091 to carry out actions described herein. In certain embodiments, such software or firmware may be initially provided to the processing system 1090 by downloading from a remote system through the processing system 1090 (e.g., via network adapter 1094).

The techniques herein may be implemented by, for example, programmable circuitry (e.g. one or more microprocessors) programmed with software and/or firmware, or entirely in special-purpose hardwired (non-programmable) circuitry, or in a combination of such forms. Special-purpose hardwired circuitry may be in the form of, for example, one or more AISCs, PLDs, FPGAs, etc.

Software or firmware for use in implementing the techniques introduced here may be stored on a machine-readable storage medium and may be executed by one or more general-purpose or special-purpose programmable microprocessors. A "machine-readable storage medium", as the term is used herein, includes any mechanism that can store information in a form accessible by a machine.

A machine can also be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch, or bridge, or any machine capable of executing a set of instructions (sequential or otherwise) that specify actions to be taken by that machine.

A machine-accessible storage medium or a storage device(s) 1095 includes, for example, recordable/non-recordable media (e.g., ROM; RAM; magnetic disk storage media; optical storage media; flash memory devices; etc.), etc., or any combination thereof. The storage medium typically may be non-transitory or include a non-transitory device. In this context, a non-transitory storage medium may include a device that is tangible, meaning that the device has a concrete physical form, although the device may change its physical state. Thus, for example, non-transitory refers to a device remaining tangible despite this change in state.

The term "logic", as used herein, may include, for example, programmable circuitry programmed with specific software and/or firmware, special-purpose hardwired circuitry, or a combination thereof.

The above specification, examples, and data provide a complete description of the manufacture and use of the composition of the invention. Since many embodiments of the invention can be made without departing from the spirit and scope of the invention, the invention resides in the claims hereinafter appended.

I claim:

1. A machine-implemented method comprising:
   establishing, in a processor, a subject identity standard for determining an identity of a subject for a regimen of administering a medication;
   establishing, in said processor, a medication administration standard for determining administration of said medication associated with said subject identity standard, comprising:
      a subject face appearance of a subject face of said subject;
      a medication appearance of said medication; and
      an image proximity of said subject face and said medication;
   establishing, in said processor, a medication regimen standard for determining compliance with said regimen of administering said medication associated with said subject identity standard;
   observing for a transmission from a mobile electronic device in said processor;
   responsive to said transmission being observed:
      receiving said transmission in said processor;
      determining whether said transmission satisfies said subject identity standard in said processor;
      determining whether said transmission satisfies said medication administration standard in said processor, comprising:
         identifying a digital image in said transmission;
         executing face recognition of said digital image in said processor to determine whether said subject face is present therein;
         executing object recognition of said digital image in said processor to determine whether said medication is present therein; and
         determining from said digital image in said processor that said medication appears proximate said subject face therein;
      determining whether said transmission satisfies said medication regimen standard in said processor; and
   responsive to said transmission satisfying said subject identity standard, said medication administration standard, and said medication regimen standard, executing a satisfaction reaction comprising recording in a data store in communication with said processor that said medication has been administered according to said regimen, and at least a portion of said transmission as evidence that said medication has been administered.

2. The method of claim 1, wherein:
said subject identity standard comprises a received alphanumeric identifier matching a standard alphanumeric identifier.

3. The method of claim 1, wherein:
said subject identity standard comprises a received biometric substantially matching a biometric standard.

4. The method of claim 1, wherein:
said medication administration standard comprises receiving said transmission.

5. The method of claim 1, wherein:
said medication administration standard comprises said transmission comprising content.

6. The method of claim 1, wherein:
said medication administration standard comprises said transmission comprising at least one of text content, image content, sound content, and video content.

7. The method of claim 5, wherein:
said medication administration standard comprises said content evidencing administering said medication.

8. The method of claim 1, wherein:
said medication regimen standard comprises at least one of a received time substantially matching a time standard, a received location substantially matching a location standard, a received medical condition substantially matching a medical condition standard, a received subject action substantially matching a subject action standard and a received environmental information substantially matching a received environmental information standard.

9. The method of claim 1, wherein:
said transmission comprises at least one of a text message, an image message, an audio message, and a video message.

10. The method of claim 1, comprising:
receiving said transmission wirelessly.

11. The method of claim 10, comprising:
receiving said transmission through a cellular network.

12. The method of claim 1, wherein:
determining whether said transmission satisfies said subject identity standard comprises evaluating metadata of said transmission.

13. The method of claim 1, wherein:
determining whether said transmission satisfies said subject identity standard comprises evaluating a content of said transmission.

14. The method of claim 1, wherein:
determining whether said transmission satisfies said subject identity standard comprises:
 obtaining a received alphanumeric identifier from said transmission; and
 comparing said received alphanumeric identifier with said alphanumeric identifier standard.

15. The method of claim 1, wherein:
determining whether said transmission satisfies said subject identity standard comprises:
 obtaining a received biometric from said transmission; and
 comparing said received biometric with said biometric standard.

16. The method of claim 1, wherein:
determining whether said transmission satisfies said medication administration standard comprises at least one of evaluating metadata of said transmission, evaluating a content of said transmission, determining receipt of said transmission, and determining whether said transmission comprises content.

17. The method of claim 1, wherein:
determining whether said transmission satisfies said medication administration standard comprises determining whether said content evidences said medication administration.

18. The method of claim 1, wherein:
determining whether said transmission satisfies said medication administration standard comprises action recognition.

19. The method of claim 1, wherein:
determining whether said transmission satisfies said medication administration standard comprises action recognition of administering said medication in content of said transmission.

20. The method of claim 1, wherein:
determining whether said transmission satisfies said medication regimen standard comprises at least one of evaluating metadata of said transmission, evaluating a content of said transmission, determining whether a time in said transmission substantially matches a time standard, determining whether a transmission time of said transmission substantially matches a time standard, determining whether a content creation time of content of said transmission substantially matches a time standard, determining whether a location in said transmission substantially matches a location standard, determining whether a transmission source location of said transmission substantially matches a location standard, determining whether a content creation location of content of said transmission substantially matches a location standard, determining whether a medical condition in said transmission substantially matches a medical condition standard, determining whether an environmental condition in said transmission substantially matches an environmental condition standard, and determining whether an environmental condition in said transmission substantially matches an environmental condition standard.

21. The method of claim 1, wherein:
determining whether said transmission satisfies said medication regimen standard comprises at least one of image recognition, object recognition, and action recognition.

22. The method of claim 1, wherein:
said satisfaction reaction comprises at least one of recording in a data store a satisfaction of said subject identity standard, said medication administration standard, and said medication regimen standard, recording in a data store at least a portion of a content of said transmission, and recording in a data store at least a portion of metadata of said transmission.

23. The method of claim 1, wherein:
said satisfaction reaction comprises outputting a satisfaction response.

24. The method of claim 23, wherein:
said satisfaction response comprises at least one of at least a portion of a content of said transmission, at least a portion of a content of said transmission, at least a portion of metadata of said transmission, outputting said satisfaction response to said subject, and outputting said satisfaction response to at least one of a caregiver of said subject, a medical entity, a research entity, an insurance entity, a regulatory entity, and a data storage entity.

25. The method of claim 23, comprising:
outputting said satisfaction response wirelessly.

26. The method of claim 25, comprising:
outputting said satisfaction response through a cellular network.

27. The method of claim 1, wherein:
if said transmission is not observed, executing a non-satisfaction reaction.

28. The method of claim 27, wherein:
said non-satisfaction reaction comprises outputting a non-satisfaction response.

29. The method of claim 27 wherein:
said non-satisfaction response comprises at least one of a reminder to said subject to administer said medication and a reminder to said subject to send said transmission.

30. The method of claim 28, comprising:
outputting said non-satisfaction response to at least one of a caregiver of said subject, a medical entity, a research entity, an insurance entity, a regulatory entity, and a data storage entity.

31. The method of claim 1, wherein:
if said transmission does not satisfy at least one of said subject identity standard, said medication administration standard, and said medication regimen standard, executing a non-satisfaction reaction.

32. The method of claim 31, wherein:
said non-satisfaction reaction comprises outputting a non-satisfaction response.

33. The method of claim 32, comprising:
outputting said non-satisfaction response to at least one of a caregiver of said subject, a medical entity, a research entity, an insurance entity, a regulatory entity, and a data storage entity.

34. An apparatus, comprising:
a processor;
a receiver in communication with said processor;
an outputter in communication with said processor;
an establisher comprising executable instructions instantiated on said processor, said establisher being adapted to
 establish a subject identity standard for determining an identity of a subject for a regimen of administering a medication,
 establish a medication administration standard for determining administration of said medication associated with said subject identity standard, comprising:
  a subject face appearance of a subject face of said subject,
  a medication appearance of said medication, and
  an image proximity of said subject face and said medication, and
 establish a medication regimen standard for determining compliance with said regimen of administering said medication associated with said subject identity standard;
a determiner comprising executable instructions instantiated on said processor, said determiner being adapted to
 determine whether a transmission satisfies said subject identity standard,
 determine whether said transmission satisfies said medication administration standard, comprising:
  identifying a digital image in said transmission,
  executing face recognition of said digital image to determine whether said subject face is present therein,
  executing object recognition of said digital image to determine whether said medication is present therein, and
  determine from said digital image that said medication appears proximate said subject face therein, and
 determine whether said transmission satisfies said medication regimen standard;
a reactor comprising executable instructions instantiated on said processor, said responder being adapted to execute a satisfaction reaction responsive to said transmission satisfying said subject identity standard, said medication administration standard, and said medication regimen standard.

35. The apparatus of claim 34, wherein:
said processor, said receiver, and said outputter comprise a portable electronic device.

36. The apparatus of claim 34, wherein:
said processor, said receiver, and said outputter comprise a portable communication device.

37. The apparatus of claim 34, wherein:
said processor, said receiver, and said outputter comprise at least one of a computer server, desktop computer, a laptop computer, a tablet, a cell phone, and a head mounted display.

38. The apparatus of claim 34, further comprising:
an observer comprising executable instructions instantiated on said processor, said observer being adapted to observe a presence of said transmission.

39. The apparatus of claim 38, wherein:
said responder is further adapted to execute a non-satisfaction reaction responsive to said observer not observing said presence of said transmission.

40. The apparatus of claim 38, wherein:
said responder is further adapted to execute a non-satisfaction reaction responsive to said transmission not satisfying at least one of said subject identity standard, said medication administration standard, and said medication regiment standard.

41. The apparatus of claim 34, wherein:
said outputter comprises at least one of a data store, a wireless transmitter, and a display.

42. The apparatus of claim 34, wherein:
said receiver comprises at least one of a sensor, a wireless receiver, and a keypad.

43. A method comprising:
establishing a subject identity standard for determining an identity of a subject for a regimen of administering a medication in a processor;
establishing a medication administration standard for determining administration of said medication associated with said subject identity standard in said processor, comprising:
 a subject face appearance of a subject face of said subject,
 a medication appearance of said medication, and
 an image proximity of said subject face and said medication;
establishing a medication regimen standard for determining compliance with said regimen of administering said medication associated with said subject identity standard in said processor;

administering said medication;
generating a transmission of administering said medication;
communicating said transmission to said processor;
determining in said processor whether said transmission satisfies said subject identity standard;
determining in said processor whether said transmission satisfies said medication administration standard, comprising:
 identifying a digital image in said transmission,
 executing face recognition of said digital image in said processor to determine whether said subject face is present therein,
 executing object recognition of said digital image in said processor to determine whether said medication is present therein, and
 determining from said digital image that said medication appears proximate said subject face therein;
determining in said processor whether said transmission satisfies said medication regimen standard; and
responsive to said transmission satisfying said subject identity standard, said medication administration standard, and said medication regimen standard, executing a satisfaction reaction with said processor.

44. The method of claim 43, wherein:
generating said transmission comprises capturing said digital image with a portable electronic device.

45. The method of claim 43, wherein:
generating said transmission of said therapeutic event comprises capturing said digital image with a smart phone.

46. The method of claim 43, wherein:
generating said transmission comprises capturing said digital image with a wearable electronic device.

47. The method of claim 43, wherein:
generating said transmission comprises capturing said digital image with a wrist mounted device, said wrist mounted device comprising an imager disposed on a palm side of a wrist of a wearer thereof and comprising a field of view encompassing at least a portion of a palm of said wearer.

48. The method of claim 43, wherein:
generating said transmission comprises capturing said digital image with a head mounted device, said head mounted device comprising an imager disposed on a forward aspect of a head of a wearer thereof and comprising a field of view encompassing at least a portion of a hand of said wearer.

* * * * *